(12) United States Patent
Jones et al.

(10) Patent No.: US 7,867,780 B2
(45) Date of Patent: Jan. 11, 2011

(54) LATERAL FLOW FORMAT, MATERIALS AND METHODS

(75) Inventors: Kevin D. Jones, Boonton, NJ (US); David Cox, Nottingham (GB)

(73) Assignee: Whatman, Inc., Elorham Park, NJ (US)

( * ) Notice: Subject to any disclaimer, the term of this patent is extended or adjusted under 35 U.S.C. 154(b) by 508 days.

(21) Appl. No.: 11/095,989

(22) Filed: Mar. 30, 2005

(65) Prior Publication Data
US 2006/0040408 A1   Feb. 23, 2006

Related U.S. Application Data

(60) Provisional application No. 60/557,851, filed on Mar. 30, 2004.

(51) Int. Cl.
    *G01N 33/53*   (2006.01)
(52) U.S. Cl. .................. 436/514; 436/518; 436/63; 436/805; 436/810; 435/287.1; 435/287.2; 435/81; 435/97; 422/56; 422/60; 422/61
(58) Field of Classification Search .............. 436/514, 436/518, 63, 805, 810; 435/287.1, 81, 287.2, 435/97; 422/56–61
See application file for complete search history.

(56) References Cited

U.S. PATENT DOCUMENTS

| 3,035,965 | A | * | 5/1962 | Mathews ................ 162/145 |
| 4,313,734 | A | | 2/1982 | Leuvering |
| 4,477,575 | A | | 10/1984 | Vogel et al. |
| 4,703,017 | A | | 10/1987 | Campbell et al. |
| 4,943,522 | A | * | 7/1990 | Eisinger et al. ........... 435/7.25 |
| 4,981,786 | A | * | 1/1991 | Dafforn et al. ........... 435/7.92 |
| 5,075,078 | A | | 12/1991 | Osikowicz et al. |
| 5,141,850 | A | | 8/1992 | Cole et al. |
| 5,160,486 | A | | 11/1992 | Schlipfenbacher et al. |
| 5,213,965 | A | * | 5/1993 | Jones ........................ 435/11 |
| 5,275,785 | A | | 1/1994 | May et al. |

(Continued)

FOREIGN PATENT DOCUMENTS

CA    2009111 A1    8/1990

(Continued)

OTHER PUBLICATIONS

Millipore, A Short Guide to Developing Immunochromatographic Test Strep, pp. 1-36 (1996).

(Continued)

*Primary Examiner*—Bao-Thuy L Nguyen
(74) *Attorney, Agent, or Firm*—Edwards Angell Palmer & Dodge LLP; David G. Conlin, Esq.; Kathryn A. Piffat, Esq.

(57) ABSTRACT

The present invention provides a lateral flow format and materials and methods for using the format in a variety of applications. More particularly, the present invention provides single-layer lateral flow formats, materials and methods for detecting the presence of an analyte using a test strip comprising a dry porous medium comprising a single hydrophilic matrix. Devices are also provided as well as methods of making and using the format. The format is particularly useful for diagnosis of physiological and genetic conditions. In addition, the present invention provides methods and materials for concentrating a reagent in a porous medium.

59 Claims, 6 Drawing Sheets

U.S. PATENT DOCUMENTS

| | | | |
|---|---|---|---|
| 5,559,041 A * | 9/1996 | Kang et al. | 436/518 |
| 5,602,040 A | 2/1997 | May et al. | |
| 5,622,871 A | 4/1997 | May et al. | |
| 5,656,503 A | 8/1997 | May et al. | |
| 5,789,261 A * | 8/1998 | Schwartz | 436/518 |
| 5,807,752 A | 9/1998 | Brizgys et al. | |
| 5,939,331 A | 8/1999 | Burd et al. | |
| 6,130,100 A | 10/2000 | Jobling et al. | |
| 6,133,048 A | 10/2000 | Penfold et al. | |
| 6,156,271 A | 12/2000 | May | |
| 6,228,660 B1 | 5/2001 | May et al. | |
| 6,352,862 B1 | 3/2002 | Davis et al. | |
| 6,451,619 B1 | 9/2002 | Catt et al. | |
| 6,670,453 B2 | 12/2003 | Frenken et al. | |
| 7,098,040 B2 * | 8/2006 | Kaylor et al. | 436/514 |
| 2003/0175991 A1 | 9/2003 | Ho et al. | |

FOREIGN PATENT DOCUMENTS

| | | |
|---|---|---|
| EP | 0381173 A2 | 8/1990 |
| EP | 0381173 A3 | 8/1990 |
| GB | 2 204 398 A | 11/1988 |
| JP | 02261395 A | 10/1990 |
| JP | 07325085 A | 12/1995 |
| JP | 8-501628 T | 2/1996 |
| JP | 08220097 A | 8/1996 |
| JP | 09178748 A | 7/1997 |
| WO | WO-88/08534 | 11/1988 |
| WO | WO 94/07136 A1 | 3/1994 |
| WO | WO 01/57522 A2 | 8/2001 |

OTHER PUBLICATIONS

Surr F., Whatman Fusion 5™ One Material, Five Functions, March 2004** (URL:http://64.233.183.104/search?q=cache:F10-kHUdxqgJ:www.whatman.com/References/WhatmanFusion5.pdf+fusion+5+membrane&hl=en&ct=clnk&cd=1&gl=nl&client=firefox-a>[pnlinel].

Correspondence (March 10, 2010) from Robert Goodayle of Whatman Intl. Ltd. (part of GE Healthcare) with attachment, Surr F., Whatman FUSION 5™ One Material, Five Functions (URL:http://64.233.183.104/search?g=cache:F10- kHUdxqgJ:www.whatman.com/References/WhatmanFusion5.pdf+fusion+5+membrane&hl=en &ct=clnk&cd=1&gl=nl&client=firefox-a>[Online]).

Millipore, a Short Guide to Developing Immunochromatographic Test Strep, pp. 1-36 (1996).

* cited by examiner

LATERAL FLOW FORMAT, MATERIALS AND METHODS

CROSS-REFERENCES TO RELATED APPLICATIONS

The present application claims priority of U.S. Provisional Application 60/557,851, filed on Mar. 30, 2004, the disclosure of which is incorporated herein by reference.

FIELD OF THE INVENTION

The present invention provides a lateral flow format and materials and methods for using the format in a variety of applications.

BACKGROUND OF THE INVENTION

A typical lateral flow test utilizes the concept of lateral liquid or suspension flow in order to transport a given sample to the test. These types of tests are used for a wide variety of applications, including diagnostics (e.g., pregnancy and other types of medical testing) and environmental testing.

Typically, a lateral flow test may require as many as five separate materials in order to optimize the test. The materials serve as a wick to transport the sample to the test; as a filtration material to remove unwanted particles; as a conjugate release pad where the detection reagent(s) is immobile when dry but mobilized when wet; as a reaction matrix where the capture reagents are immobilized; and as an absorbent where the sample is absorbed and the liquid is driven to flow along the test format.

Despite the wide array of usages, lateral flow tests are frequently subject to flow problems and are complicated to manufacture. These tests are complex, multipart assays performed on a series of overlapping pads of different types of materials aligned on a test strip. Problems arise from material incompatibility, contact issues, and imperfect material characteristics. Boundaries found between segments can adversely affect flow characteristics. Different materials may have widely different flow, or wicking, rates and may have different effects on molecules flowing through them.

Currently, different materials are used for each part of the test, due to the vastly different physical characteristics needed for each component. For example, the sample wick must be fast wicking and have a very open structure; the filtration material must have a pore size of the correct size to remove the unwanted particles; the conjugate release must be non-protein binding; the reaction matrix must be protein binding and consistent. Due to the different properties required, it is normal for a test to be made up of overlapping pads of several different materials. Generally, a membrane, such as a nitrocellulose membrane, is used for the reaction matrix; glass fiber or man-made fibers (e.g., cellulose) are used for the sample application/filtration layer and for the conjugate release layer; and cellulose or glass fiber materials are used for the absorbent (Whatman plc).

Typically, a sample is placed on a sample application wick (e.g., glass fiber, cast cellulose acetate, fused PE, or cellulose fiber), where the wicking process begins. Optionally, the sample runs through the wick and into and through a filtration pad (e.g., glass fiber, glass membrane, cellulose fiber, cast cellulose acetate, fused PE, man-made fibers, and mixtures of man-made fibers and glass fibers), which may be used to remove contaminants or, for example, to remove erythrocytes (red blood cells) in a blood sample in order to eliminate them from the sample or to prevent their red coloration from interfering with a downstream color indicator. Next, the sample wicks into a conjugate pad (e.g., glass fiber or polyester), where the sample liquid or suspension mixes with the colored conjugate reagent (e.g., an antibody), causing the conjugate reagent to be released. If the sample is positive, the conjugate will bind to the analyte. Both bound and unbound conjugate will flow laterally through the conjugate pad into capture area pad, which is typically nitrocellulose. In some examples, the capture area pad may comprise two lines of protein striped perpendicularly onto the nitrocellulose membrane. One line (test) binds to the analyte (if present), while the other (control) binds to the conjugate in order to indicate that the test itself has been successful, regardless of positive or negative result. Therefore, a successful positive test shows two lines (test and control), while a successful negative test shows one line (control only). The absorbent pad, which is typically cellulose or glass fiber, acts as an absorbent to pull the liquid through the strip. The entire assembly of overlapping pads, each having one or more layers, is attached to an assembly sheet, which may be made of various types of materials (e.g., plastic) and which does not interact with the test.

It would be desirable to have a single-layer lateral flow format to reduce flow problems due to material incompatibility and contact issues, to decrease development time, to improve accuracy and efficiency of lateral flow test results, to provide superior performance, to lower manufacturing costs, and to aid in the ease of use of the format.

SUMMARY OF THE INVENTION

In one aspect, the present invention provides a test strip for detecting the possible presence of an analyte in a liquid sample applied to the test strip, the test strip comprising a dry porous medium comprising a single hydrophilic matrix, wherein the single hydrophilic matrix comprises:

a. a network of fibers; and
b. a series of zones comprising:
  i. a sample application zone;
  ii. a conjugate release zone comprising a labeled binding reagent, wherein
    the labeled binding reagent specifically binds to the analyte to form a first complex comprising the labeled binding reagent and the analyte;
    the labeled binding reagent comprises a label; and
    the labeled binding reagent is dry on the test strip prior to application of the liquid sample and is released into mobile form upon contact with the liquid sample; and
  iii. a capture test zone comprising a capture test reagent, wherein
    the capture test reagent specifically binds either to the analyte or to the first complex to form a second complex comprising the labeled binding reagent, the analyte, and the capture test reagent; and
    the capture test reagent is dry on the test strip prior to application of the liquid sample and is largely immobile.

In another aspect, the present invention provides a test strip for detecting the possible presence of an analyte in a liquid sample applied to the test strip, the test strip comprising a dry porous medium comprising a single hydrophilic matrix, wherein the single hydrophilic matrix comprises:

a. a network of fibers; and
b. a series of zones comprising:

i. a sample application zone;
ii. a conjugate release zone, preferably comprising a labeled binding reagent, wherein
the labeled binding reagent specifically binds to the analyte to form a first complex comprising the labeled binding reagent and the analyte;
the labeled binding reagent comprises a label; and
the labeled binding reagent is dry on the test strip prior to application of the liquid sample and is released into mobile form upon contact with the liquid sample;
iii. a capture test zone, preferably comprising a capture test reagent, wherein
the capture test reagent specifically binds either to the analyte or to the first complex to form a second complex comprising the labeled binding reagent, the analyte, and the capture test reagent; and
the capture test reagent is dry on the test strip prior to application of the liquid sample and is largely immobile;
iv. a capture control zone, preferably comprising a capture control reagent, wherein
the capture control reagent binds to the labeled binding reagent to form a third complex comprising the labeled binding reagent and the capture control reagent; and
the capture control reagent is dry on the test strip prior to application of the liquid sample and is largely immobile; and
v. an absorbent zone, wherein the absorbent zone draws the liquid sample through the dry porous medium of the test strip by capillary action.

In another aspect, the present invention provides a device for detecting the possible presence of an analyte in a liquid sample, wherein the device comprises:
a. the test strip described above;
b. a housing containing the test strip, wherein the housing comprises at least one opening to expose the surface of the test strip in the application zone for application of the liquid sample.

In another aspect, the present invention provides a test strip for detecting the possible presence of an analyte in a liquid sample applied to the test strip, the test strip comprising a dry porous medium comprising a single hydrophilic matrix, wherein the single hydrophilic matrix comprises:
a. a monolithic hydrophilic matrix comprising a network of fibers; and
b. a series of zones comprising:
i. a sample application zone;
ii. a conjugate release zone comprising a labeled binding reagent, wherein
the labeled binding reagent comprises:
a label;
a solid substrate comprising a carrier bead, wherein the carrier bead is mobile within the matrix when the carrier bead and matrix are wet; and
a ligand that specifically binds to the analyte to form a first complex comprising the labeled binding reagent and the analyte; and
the labeled binding reagent is dry on the test strip prior to application of the liquid sample and is released into mobile form upon contact with the liquid sample;
iii. a capture test zone comprising a capture test reagent, wherein
the capture test reagent comprises:
a solid substrate comprising a capture test bead; and
a ligand that specifically binds to the analyte or to the first complex to form a second complex comprising the labeled binding reagent, the analyte, and the capture reagent; and
the capture test reagent is dry on the test strip prior to application of the liquid sample and is substantially immobile;
iv. a capture control zone comprising a capture control reagent, wherein
the capture control reagent comprises:
a solid substrate comprising a capture control bead; and
a ligand that specifically binds to the labeled binding reagent to form a third complex comprising the labeled binding reagent and the capture control reagent; and
the capture control reagent is dry on the test strip prior to application of the liquid sample and is substantially immobile; and
v. an absorbent zone, wherein the absorbent zone draws the liquid sample through the dry porous medium of the test strip by capillary action.

In another aspect, the present invention provides a method for making a test strip for detecting the possible presence of an analyte in a liquid sample applied to the test strip, the test strip comprising a dry porous medium comprising a single hydrophilic matrix comprising a monolithic hydrophilic matrix, wherein the method comprises:
a. providing a monolithic hydrophilic matrix, wherein the monolithic hydrophilic matrix comprises a network of fibers;
b. creating a conjugate release zone on the monolithic hydrophilic matrix by:
i. providing a labeled binding reagent, wherein the labeled binding reagent comprises:
a label;
a solid substrate comprising a carrier bead, wherein the carrier bead is mobile within the matrix when the carrier bead and matrix are wet; and
a ligand that specifically binds to the analyte to form a first complex comprising the labeled binding reagent and the analyte; and
ii. suspending the labeled binding reagent in a buffer;
iii. applying the labeled binding reagent suspension to a first zone of the monolithic hydrophilic matrix;
c. creating a capture test zone on the monolithic hydrophilic matrix by:
i. providing a capture test reagent, wherein the capture test reagent comprises:
a solid substrate comprising a capture test bead;
a ligand that specifically binds to the analyte or to the first complex to form a second complex comprising the labeled binding reagent, the analyte, and the capture test reagent; and
ii. suspending the capture test reagent in a buffer;
iii. applying the capture test reagent suspension to a second zone of the monolithic hydrophilic matrix, wherein the second zone is downstream from the first zone; and d. creating a capture control zone on the monolithic hydrophilic matrix by:
  i. providing a capture control reagent, wherein the capture control reagent comprises:
    a solid substrate comprising a capture control bead; and
    a ligand that binds to the labeled binding reagent to form a third complex comprising the labeled binding reagent and the capture control reagent; and
  ii. suspending the capture control reagent in a buffer;
  iii. applying the capture control reagent suspension to a third zone of the monolithic hydrophilic matrix, wherein the third zone is downstream from the second zone; and
e. drying the monolithic hydrophilic matrix to yield a dry porous medium.

In still another aspect of the invention, the present invention provides a method of using a test strip to detect the possible presence of an analyte in a liquid sample applied to the test strip, wherein the method comprises:

a. providing a test strip comprising a dry porous medium comprising a single hydrophilic matrix, wherein the single hydrophilic matrix comprises:
  i. a monolithic hydrophilic matrix comprising a network of fibers; and
  ii. a series of zones comprising:
    (a) a sample application zone;
    (b) a conjugate release zone comprising a labeled binding reagent, wherein
      (i) the labeled binding reagent comprises:
        a label;
        a solid substrate comprising a carrier bead, wherein the carrier bead is mobile within the matrix when the carrier bead and matrix are wet; and
        a ligand that specifically binds to the analyte to form a first complex comprising the labeled binding reagent and the analyte; and
      (ii) the labeled binding reagent is dry on the test strip prior to application of the liquid sample and is released into mobile form upon contact with the liquid sample;
    (c) a capture test zone comprising a capture test reagent, wherein
      (i) the capture test reagent comprises:
        a solid substrate comprising a capture test bead; and
        a ligand that specifically binds to the analyte or to the first complex to form a second complex comprising the labeled binding reagent, the analyte, and the capture reagent; and
      (ii) the capture test reagent is dry on the test strip prior to application of the liquid sample and is substantially immobile;
    (d) a capture control zone comprising a capture control reagent, wherein
      (i) the capture control reagent comprises:
        a solid substrate comprising a capture control bead; and
        a ligand that specifically binds to the labeled binding reagent to form a third complex comprising the labeled binding reagent and the capture control reagent; and
      (ii) the capture control reagent is dry on the test strip prior to application of the liquid sample and is substantially immobile; and
    (e) an absorbent zone, wherein the absorbent zone draws the liquid sample through the dry porous medium of the test strip by capillary action;
b. obtaining a liquid sample;
c. applying the liquid sample to the sample application zone of the test strip;
d. wicking the liquid sample through the single hydrophilic matrix to the conjugate release zone;
e. contacting the labeled binding reagent with the liquid sample to mobilize the labeled binding reagent and to permit formation of the first complex if the liquid sample comprises analyte;
f. wicking the liquid sample and the labeled binding reagent, whether alone or in the first complex, through the single hydrophilic matrix to the capture test zone;
g. contacting the capture test reagent with the liquid sample and the labeled binding reagent, whether alone or in the first complex, to permit formation of the second complex if the first complex is present;
h. concentrating the second complex in the network of fibers in the capture test zone of the single hydrophilic matrix;
i. detecting the presence of the second complex in the capture test zone;
j. wicking the liquid sample and the labeled binding reagent through the single hydrophilic matrix to the capture control zone;
k. contacting the capture control reagent with the liquid sample and the labeled binding reagent to permit formation of the third complex;
l. concentrating the third complex in the network of fibers in the capture control zone of the single hydrophilic matrix; and
m. detecting the presence of the third complex in the capture control zone.

In yet another aspect, the present invention provides a method of diagnosing disease, a phenotype, a genotype, or a physiological condition in an organism by detecting the presence of an analyte associated with the disease, the phenotype, the genotype, or the physiological condition in a liquid biological sample, wherein the method comprises:

a. providing a test strip comprising a dry porous medium comprising a single hydrophilic matrix, wherein the single hydrophilic matrix comprises:
  i. a monolithic hydrophilic matrix comprising a network of fibers; and
  ii. a series of zones comprising:
    (a) a sample application zone;
    (b) a conjugate release zone comprising a labeled binding reagent, wherein
      (i) the labeled binding reagent comprises
        a label;
        a solid substrate comprising a carrier bead, wherein the carrier bead is mobile within the matrix when the carrier bead and matrix are wet; and
        a ligand that specifically binds to the analyte to form a first complex comprising the labeled binding reagent and the analyte; and
      (ii) the labeled binding reagent is dry on the test strip prior to application of the liquid sample and is released into mobile form upon contact with the liquid sample;

(c) a capture test zone comprising a capture test reagent, wherein
   (i) the capture test reagent comprises:
      a solid substrate comprising a capture test bead; and
      a ligand that specifically binds to the analyte or to the first complex to form a second complex comprising the labeled binding reagent, the analyte, and the capture reagent; and
   (ii) the capture test reagent is dry on the test strip prior to application of the liquid sample and is substantially immobile;
(d) a capture control zone comprising a capture control reagent, wherein
   (i) the capture control reagent comprises:
      a solid substrate comprising a capture control bead; and
      a ligand that specifically binds to the labeled binding reagent to form a third complex comprising the labeled binding reagent and the capture control reagent; and
   (ii) the capture control reagent is dry on the test strip prior to application of the liquid sample and is substantially immobile; and
(e) an absorbent zone, wherein the absorbent zone draws the liquid sample through the dry porous medium of the test strip by capillary action;

b. obtaining a liquid biological sample from an organism;
c. applying the liquid biological sample to the sample application zone of the test strip;
d. wicking the liquid biological sample through single hydrophilic matrix to the conjugate release zone;
e. contacting the labeled binding reagent with the liquid biological sample to mobilize the labeled binding reagent and to permit formation of the first complex;
f. wicking the liquid biological sample, the labeled binding reagent, and the first complex through the single hydrophilic matrix to the capture test zone;
g. contacting the capture test reagent with the liquid biological sample, the labeled binding reagent, and the first complex to permit formation of the second complex;
h. concentrating the second complex in the network of fibers in the capture test zone of the single hydrophilic matrix;
i. detecting the presence of the second complex in the capture test zone;
j. wicking the liquid sample and the labeled binding reagent through the single hydrophilic matrix to the capture control zone;
k. contacting the capture control reagent with the liquid sample and the labeled binding reagent to permit formation of the third complex;
l. concentrating the third complex in the network of fibers in the capture control zone of the single hydrophilic matrix;
m. detecting the presence of the third complex in the capture control zone; and
n. diagnosing the disease, the phenotype, the genotype, or the physiological condition of the organism.

In another aspect, the present invention provides a test strip for detecting the possible presence of any one of multiple analytes in a liquid sample applied to the test strip, the test strip comprising a dry porous medium comprising a single hydrophilic matrix, wherein the single hydrophilic matrix comprises:

a. a monolithic hydrophilic matrix comprising a network of fibers; and
b. a series of zones comprising:
   i. a sample application zone;
   ii. a conjugate release zone comprising a plurality of labeled binding reagents, wherein
      (a) each labeled binding reagent comprises:
         (i) a label;
         (ii) a solid substrate comprising a carrier bead, wherein the carrier bead is mobile within the matrix when the carrier bead and matrix are wet; and
         (iii) a ligand that specifically binds to one of the analytes to form a first complex comprising the labeled binding reagent and the analyte;
      (b) each labeled binding reagent is dry on the test strip prior to application of the liquid sample and is released into mobile form upon contact with the liquid sample; and
      (c) each labeled binding reagent specifically binds to a different analyte among the multiple analytes of the test;
   iii. a capture test zone comprising a plurality of capture test reagents, wherein:
      (a) each capture test reagent comprises:
         (i) a solid substrate comprising a capture test bead; and
         (ii) a ligand that specifically binds to one of the analytes or to one of the first complexes to form a second complex comprising the labeled binding reagent, analyte, and the capture reagent;
      (b) each capture test reagent is dry on the test strip prior to application of the liquid sample and is substantially immobile; and
      (c) each capture test reagent specifically binds to a different analyte or first complex among the multiple analytes and first complexes of the test;
   iv. a capture control zone comprising at least one capture control reagent, wherein
      (a) the capture control reagent comprises:
         (i) a solid substrate comprising a capture control bead; and
         (ii) a ligand that specifically binds to the labeled binding reagent to form a third complex comprising the labeled binding reagent and the capture control reagent; and
      (b) the capture control reagent is dry on the test strip prior to application of the liquid sample and is substantially immobile; and
   v. an absorbent zone, wherein the absorbent zone draws the liquid sample through the dry porous medium of the test strip by capillary action.

In another aspect, the present invention provides test strip for a competitive assay for detecting the possible presence of an analyte in a liquid sample applied to the test strip, the test strip comprising a dry porous medium comprising a single hydrophilic matrix, wherein the single hydrophilic matrix comprises:

a. a monolithic hydrophilic matrix comprising a network of fibers; and
b. a series of zones comprising:
   i. a sample application zone;
   ii. a conjugate release zone comprising a labeled binding reagent, wherein
      (a) the labeled binding reagent comprises:
         (i) a label;
         (ii) a solid substrate comprising a carrier bead, wherein the carrier bead is mobile within the matrix when the carrier bead and matrix are wet; and
         (iii) a ligand that specifically binds to the analyte to form a first complex comprising the labeled binding reagent and the analyte; and
      (b) the labeled binding reagent is dry on the test strip prior to application of the liquid sample and is released into mobile form upon contact with the liquid sample;
   iii. a capture test zone comprising a capture test reagent, wherein:
      (a) the capture test reagent comprises:
         (i) a solid substrate comprising a capture test bead; and
         (ii) a ligand comprising either the analyte or an analog of the analyte; and
      (b) the capture test reagent is dry on the test strip prior to application of the liquid sample and is substantially immobile;
   iv. a capture control zone comprising a capture control reagent, wherein
      (a) the capture control reagent comprises:
         (i) a solid substrate comprising a capture control bead; and
         (ii) a ligand that specifically binds to the labeled binding reagent to form a second complex comprising the labeled binding reagent and the capture control reagent; and
      (b) the capture control reagent is dry on the test strip prior to application of the liquid sample and is substantially immobile; and
   v. an absorbent zone, wherein the absorbent zone draws the liquid sample through the dry porous medium of the test strip by capillary action.

In yet a further aspect, the present invention provides a method for concentrating a reagent in a porous medium comprising a monolithic hydrophilic matrix, wherein the method comprises:
a. providing a monolithic hydrophilic matrix;
b. providing a reagent, wherein the reagent comprises:
   i. a solid substrate; and
   ii. an agglutinating agent activated upon contact with an aqueous liquid;
c. suspending the reagent in a buffer to yield a reagent suspension;
d. applying the reagent suspension to the monolithic hydrophilic matrix;
e. drying the reagent suspension on the monolithic hydrophilic matrix; and
f. applying an aqueous liquid to the porous medium to activate the agglutinating agent in order to self-agglutinate the solid substrate of the reagent for concentrating the reagent in the monolithic hydrophilic matrix of the porous medium.

In yet a further aspect, the present invention provides a method for concentrating a reagent in a porous medium comprising a monolithic hydrophilic matrix, wherein the method comprises:
a. providing a monolithic hydrophilic matrix;
b. providing a reagent, wherein the reagent comprises:
   a. a negatively-charged solid substrate;
   b. a positively-charged ligand attached to the solid substrate;
c. suspending the reagent in a buffer to yield a reagent suspension;
d. applying the reagent suspension to the monolithic hydrophilic matrix;
e. drying the reagent suspension on the monolithic hydrophilic matrix; and
f. contacting the ligand with an aqueous liquid having a pH below the pI of the ligand and comprising a substance to which the ligand binds;
g. altering the overall charge of the reagent in order to self-agglutinate the reagent for concentrating the reagent in the monolithic hydrophilic matrix of the porous medium.

DETAILED DESCRIPTION OF THE INVENTION

Figure 1A:
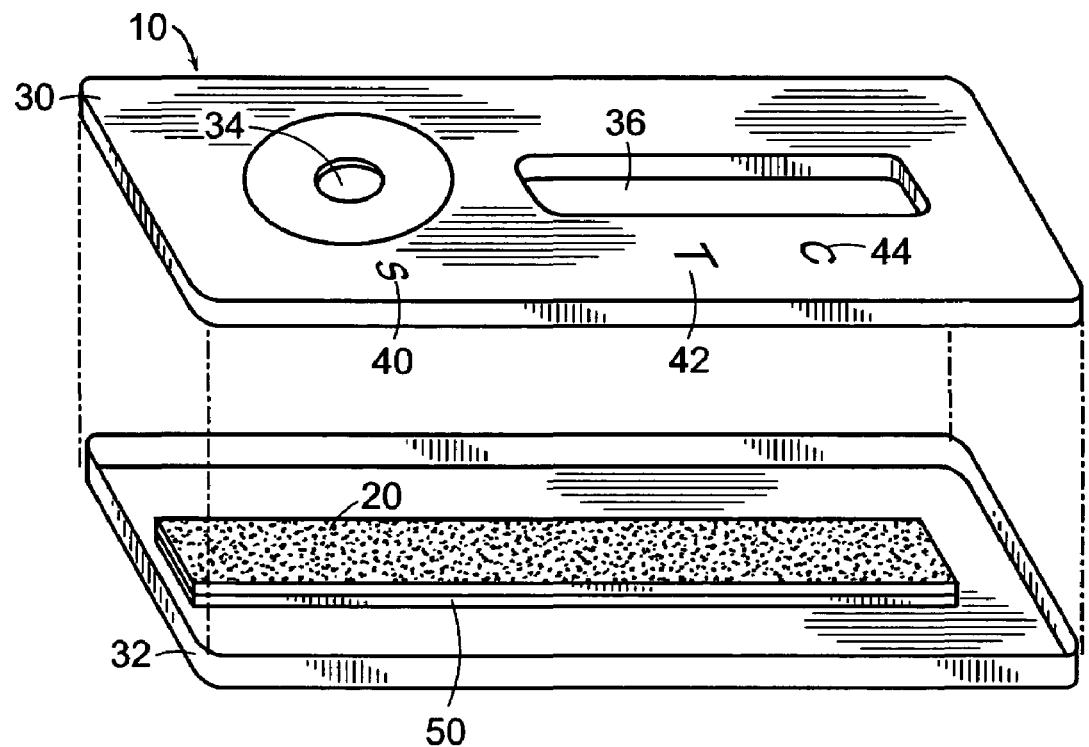
FIG. 1A depicts an exploded view of one embodiment of a single-layer lateral flow format test strip in a housing.

The present invention provides a single-layer lateral flow format and materials and methods for using the format in a variety of applications. In one aspect, the membrane of the invention is a lateral flow test strip for lateral flow assays. In one embodiment, it is a membrane for striping antibodies as test and control lines, thereby serving as the carrier for the test and control line antibodies. In one embodiment, these are conjugated to latex, which allows for the binding of the test and control line antibodies to the membrane. The membrane also serves as a conjugate release pad, maintaining the stability of the gold conjugate and allowing for good conjugate release. Lastly, the membrane serves as a sample pad where it accepts and delivers the sample/buffer to the rest of the test strip. It performs a simple filtration as it passes the analyte and buffer to the rest of the strip. A wicking material may be used to pull the buffer and analyte from the sample entry area past the conjugate, test and control lines on the test strip.

In one aspect, the present invention provides a test strip for detecting the possible presence of an analyte in a liquid sample applied to the test strip, the test strip comprising a dry porous medium comprising a single hydrophilic matrix, wherein the single hydrophilic matrix comprises:
  a. a network of fibers; and
  b. a series of zones comprising:
    i. a sample application zone;
    ii. a conjugate release zone comprising a labeled binding reagent, wherein
      the labeled binding reagent specifically binds to the analyte to form a first complex comprising the labeled binding reagent and the analyte;
      the labeled binding reagent comprises a label; and
      the labeled binding reagent is dry on the test strip prior to application of the liquid sample and is released into mobile form upon contact with the liquid sample;
    iii. a capture test zone comprising a capture test reagent, wherein
      the capture test reagent specifically binds either to the analyte or to the first complex to form a second complex comprising the labeled binding reagent, the analyte, and the capture test reagent; and
      the capture test reagent is dry on the test strip prior to application of the liquid sample and is largely immobile;
    iv. a capture control zone comprising a capture control reagent, wherein
      the capture control reagent binds to the labeled binding reagent to form a third complex comprising the labeled binding reagent and the capture control reagent; and
      the capture control reagent is dry on the test strip prior to application of the liquid sample and is largely immobile; and
    v. an absorbent zone, wherein the absorbent zone draws the liquid sample through the dry porous medium of the test strip by capillary action.

In one embodiment, the single hydrophilic matrix comprises a monolithic hydrophilic matrix.

In a preferred embodiment, the single hydrophilic matrix comprises glass, polymer, cellulose acetate, or a combination thereof.

Preferably, the glass comprises glass fiber or glass microfiber.

Preferably, the polymer comprises polyester, polyethylene, polypropylene, latex, polyether sulfone, polyvinylidene fluoride, polyethylene, nylon, polytetrafluoroethylene, or cellulose acetate. More preferably, the single hydrophilic matrix comprises a mixture of glass fiber and polymer. Still more preferably, the non-woven plastic comprises latex.

In a preferred embodiment, the single hydrophilic matrix further comprises a binder. Preferably, the binder is selected from the group consisting of polyvinylacrylamide, polyvinylacrylate, polyvinylalcohol, polystyrene, and polymethylmethacrylate, and gelatin.

In a preferred embodiment, the single hydrophilic matrix has a wicking rate of at least 4 cm in 240 seconds for water. More preferably, the single hydrophilic matrix has a wicking rate of at least 4 cm in 100 seconds for water. More preferably, the wicking rate is in the range of at least 4 cm in 60 seconds for water. Still more preferably, the wicking rate is in the range of at least 4 cm in 50 seconds for water.

In another preferred embodiment, the single hydrophilic matrix has an average pore size in the range of 1.5 microns to 25.0 microns. More preferably, the average pore size is in the range of 2.0 microns to 7.0 microns. Still more preferably, the average pore size is in the range of 3.0 microns to 6.0 microns.

In another preferred embodiment, the single hydrophilic matrix has a thickness of between 50 microns and 1000 microns. More preferably, the thickness is between 150 microns and 500 microns.

In another preferred embodiment, the labeled binding reagent further comprises a ligand that specifically binds to the analyte. More preferably, the labeled binding reagent further comprises a solid support to which the ligand is attached and the solid support comprises gold, latex, selenium, platinum, copper, or iron. Still more preferably, the solid support comprises a carrier bead. In a particularly preferred embodiment, the size of the carrier bead allows the carrier bead to move through the matrix, and the bead is mobile within the matrix when the bead and matrix are wet. More preferably, the diameter of the carrier bead is 10% or less than the average pore size of the matrix.

In a preferred embodiment,
  a. the average pore size of the matrix is in the range of 4.0 to 6.0 micrometers; and
  b. the carrier bead comprises a gold bead having a diameter in the range of 20 to 80 nanometers.

In a preferred embodiment,
  a. the average pore size of the matrix is in the range of 4.0 to 6.0 micrometers; and
  b. the carrier bead comprises a latex bead having a diameter in the range of 100 to 800 nanometers.

In a preferred embodiment, the carrier bead comprises a latex bead comprising a colorimetric dye or a fluorescent dye. In another preferred embodiment, the carrier bead comprises a latex bead comprising a paramagnetic cores, a plasmon resonant particle, or a quantum dot.

In a preferred embodiment, the label of the labeled binding reagent comprises a calorimetric indicator, a fluorescent indicator, a photometric indicator, a radioactive indicator, or an immunological indicator. More preferably, the label comprises a dye.

In a preferred embodiment, the ligand comprises:
  a. a polypeptide, an oligopeptide, an antigen, an antibody, or a prion;
  b. a nucleic acid or a peptide nucleic acid;
  c. a drug, an analog of a drug, or a drug metabolite; or
  d. an imprinted polymer.

Preferably, the nucleic acid comprises DNA, PNA, or RNA. Preferably, the DNA comprises genomic DNA, cDNA, a protein binding site, an oligonucleotide, or a primer, or the DNA comprises a protein binding site comprising a promoter element or a transcriptional activation domain. Preferably, the DNA comprises single-stranded DNA. Preferably, the RNA comprises messenger RNA (mRNA) or short interfering RNA (siRNA).

In a preferred embodiment,
  a. the analyte comprises a nucleic acid having a target sequence of interest; and
  b. the ligand comprises a nucleic acid having a sequence of at least 65% complementarity to the target sequence of interest.

Preferably, the ligand comprises a nucleic acid having a sequence of at least 75% complementarity to the target sequence of interest; more preferably, at least 85% complementarity to the target sequence of interest; still more preferably, at least 95% complementarity to the target sequence of interest; yet more preferably, at least 97% complementarity to the target sequence of interest; and even more preferably, at least 99% complementarity to the target sequence of interest.

In another preferred embodiment,
a. the analyte comprises an antigen; and
b. the ligand comprises an antibody that specifically binds to the antigen.

Alternatively,
a. the ligand comprises an antigen; and
b. the analyte comprises an antibody that specifically binds to the antigen.

In another preferred embodiment,
a. the ligand comprises an oligopeptide; and
b. the analyte comprises a protein that binds to the oligopeptide.

In still another preferred embodiment,
a. the analyte comprises a drug or an analog of a drug; and
b. the ligand comprises a protein that binds to the drug.

Alternatively,
a. the ligand comprises a drug or an analog of a drug; and
b. the analyte comprises a protein that binds to the drug.

In still another preferred embodiment,
a. the ligand comprises an imprinted polymer; and
b. the analyte comprises:
  i. a polypeptide, an oligopeptide, an antigen, an antibody, or a prion;
  ii. a nucleic acid or a peptide nucleic acid; or
  iii. a drug, an analog of a drug or a drug metabolite.

In another preferred embodiment, the capture test reagent further comprises a ligand that specifically binds to the analyte or to the first complex.

In another preferred embodiment, the capture test reagent further comprises a solid support to which the ligand is attached. Preferably, the solid support comprises latex, silica, glass, alumina, cellulose, or a sugar.

In a particularly preferred embodiment, the solid support comprises a capture test bead. Preferably, the capture test bead comprises a sulfate terminated latex bead.

In one preferred embodiment, the sulfate terminated latex bead physically binds proteins.

In another preferred embodiment, the capture test bead comprises a covalent binding latex bead.

In yet another preferred embodiment, the size of the capture test bead largely inhibits its movement through the matrix. Preferably, the size of the capture test bead is in the range of 20% to 70% of the average pore size of the matrix. More preferably, the size of the capture test bead is in the range of 30% to 60% of the average pore size of the matrix.

More preferably,
a. the average pore size of the matrix is in the range of 4.0 to 6.0 micrometers; and
b. the capture test bead comprises a latex bead having a diameter in the range of 1.5 to 2.5 nanometers.

In a preferred embodiment, the binding of the ligand to the analyte or to the first complex concentrates the labeled binding reagent to enable detection of the label indicating the presence of the second complex. Preferably, the capture test bead comprises a latex capture bead comprising an agglutinating agent. More preferably, the agglutinating agent comprises polyethylene glycol (PEG).

In a preferred embodiment, the ligand comprises:
a. a polypeptide, an oligopeptide, an antigen, or an antibody; or
b. a nucleic acid or peptide nucleic acid;
c. a drug, an analog of a drug, or a drug metabolite; or
d. an imprinted polymer.

Preferably, the nucleic acid comprises DNA, PNA, or RNA. Preferably, the DNA comprises genomic DNA, cDNA, a protein binding site, an oligonucleotide, or a primer, or the DNA comprises a protein binding site comprising a promoter element or a transcriptional activation domain. Preferably, the DNA comprises single-stranded DNA. Preferably, the RNA comprises messenger RNA (mRNA).

In a preferred embodiment,
a. the analyte comprises a nucleic acid having an exposed target sequence of interest; and
b. the ligand comprises a nucleic acid having a sequence of at least 65% complementarity to the target sequence of interest.

Preferably, the ligand comprises a nucleic acid having a sequence of at least 75% complementarity to the target sequence of interest; more preferably, at least 85% complementarity to the target sequence of interest; still more preferably, at least 95% complementarity to the target sequence of interest; yet more preferably, at least 97% complementarity to the target sequence of interest; even more preferably, at least 99% complementarity to the target sequence of interest.

In a preferred embodiment,
a. either the analyte or the first complex comprises an antigen; and
b. the ligand comprises an antibody that specifically binds to the antigen, wherein the antibody does not significantly bind to the labeled binding reagent in the absence of the analyte.

Alternatively,
a. the ligand comprises an antigen; and
b. either the analyte or the first complex comprises an antibody that specifically binds to the antigen, wherein the labeled binding reagent does not significantly bind to the antigen in the absence of the analyte.

In a preferred embodiment,
a. the ligand comprises an oligopeptide; and
b. either the analyte or the first complex comprises a protein that binds to the oligopeptide, wherein the labeled binding reagent does not significantly bind to the oligopeptide in the absence of the analyte.

In another preferred embodiment,
a. the ligand comprises an imprinted polymer; and
b. either the analyte or the first complex comprises a substance that binds to the imprinted polymer, wherein the labeled binding reagent does not significantly bind to the imprinted polymer in the absence of the analyte.

More preferably, the substance that binds to the imprinted polymer comprises a protein.

In another embodiment, the capture control reagent further comprises a ligand that specifically binds to the labeled binding reagent. Preferably, the capture control reagent further comprises a solid support to which the ligand is attached. More preferably, the solid support comprises latex, silica, glass, alumina, cellulose, or a sugar.

In a particularly preferred embodiment, the solid support comprises a capture control bead. Preferably, the capture control bead comprises a sulfate terminated latex bead. More preferably, the sulfate terminated latex bead physically binds proteins. Preferably, the capture control bead comprises a covalent binding latex bead.

In a preferred embodiment, the size of the capture control bead largely inhibits its movement through the matrix. Preferably, the size of the capture control bead is in the range of 20% to 70% of the average pore size of the matrix. More preferably, the size of the capture control bead is in the range of 30% to 60% of the average pore size of the matrix.

In a particularly preferred embodiment,
  a. the average pore size of the matrix is in the range of 4.0 to 6.0 micrometers; and
  b. the capture control bead comprises a latex bead having a diameter in the range of 1.5 to 2.5 nanometers.

In another preferred embodiment, the binding of the ligand to the labeled binding reagent concentrates the labeled binding reagent to enable detection of the label indicating the presence of the third complex. Preferably, the capture control bead comprises a latex capture bead comprising an agglutinating agent. More preferably, the agglutinating agent comprises polyethylene glycol (PEG).

In another preferred embodiment,
  a. the labeled binding reagent has an overall negative charge; and
  b. the capture control reagent has an overall positive charge.

More preferably,
  a. the labeled binding reagent comprises a negatively charged gold carrier bead; and
  b. the capture control reagent comprises:
    i. a positively charged polymer; or
    ii. a positively charged ligand.

In another preferred embodiment,
  a. the labeled binding reagent has an overall positive charge; and
  b. the capture control reagent has an overall negative charge.

In another preferred embodiment, the ligand comprises:
  a. a polypeptide, an oligopeptide, an antigen, or an antibody; or
  b. a nucleic acid or peptide nucleic acid;
  c. a drug, an analog of a drug, or a drug metabolite; or
  d. an imprinted polymer.

Preferably, the nucleic acid comprises DNA, PNA, or RNA. Preferably, the DNA comprises genomic DNA, cDNA, a protein binding site, an oligonucleotide, or a primer, or the DNA comprises a protein binding site comprising a promoter element or a transcriptional activation domain. Preferably, the DNA comprises single-stranded DNA. Preferably, the RNA comprises messenger RNA (mRNA).

In a preferred embodiment,
  a. the labeled binding reagent comprises a nucleic acid having an exposed target sequence of interest; and
  b. the ligand comprises a nucleic acid having a sequence of at least 65% complementarity to the target sequence of interest.

Preferably, the ligand comprises a nucleic acid having a sequence of at least 75% complementarity to the target sequence of interest; more preferably, at least 85% complementarity to the target sequence of interest; still more preferably, at least 95% complementarity to the target sequence of interest.

In a preferred embodiment,
  a. the labeled binding reagent comprises an antigen; and
  b. the ligand comprises an antibody that specifically binds to the antigen.

Alternatively,
  a. the ligand comprises an antigen; and
  b. the labeled binding reagent comprises an antibody that specifically binds to the antigen.

In a preferred embodiment,
  a. the ligand comprises an oligopeptide; and
  b. the labeled binding reagent comprises a protein that binds to the oligopeptide.

In another preferred embodiment,
  a. the ligand comprises an imprinted polymer; and
  b. the labeled binding reagent comprises a substance that binds to the imprinted polymer.

More preferably, the substance that binds to the imprinted polymer comprises a protein.

In another embodiment, the liquid sample comprises blood, plasma; serum; mucus; urine; saliva; semen; vaginal discharge; sweat; tears; lymph; gastrointestinal fluid, suspension or colloidal mixture; cerebrospinal fluid; a bacterial culture; a tissue culture; a phage lysate; water; a beverage; an organic solvent; an aqueous or organic solution; a suspension of cells, viruses, or other replicative entities; or a colloidal mixture.

In still another embodiment, the analyte comprises a polypeptide, an oligonucleotide, an antibody, an antigen, a prion, a nucleic acid, a peptide nucleic acid, a drug, an analog of a drug, or a drug metabolite. Preferably, the presence or absence of the analyte comprises a marker for a physiological condition. More preferably, the physiological condition comprises pregnancy, nursing, a disease, a phenotype, genotype, or a normal or abnormal physiological condition.

In another preferred embodiment, the analyte comprises a nucleic acid and the physiological condition comprises a genotype. More preferably, the nucleic acid comprises a genetic mutation or a polymorphism.

In another preferred embodiment, the analyte comprises a drug or an analog of a drug.

In a preferred embodiment,
  a. the analyte comprises an antigen from a first mammalian species; and
  b. the labeled binding reagent comprises a ligand comprising an antibody that specifically binds to the antigen, wherein the antibody is from a second mammalian species.

More preferably,
  c. the capture control reagent comprises an ligand comprising an antibody from a third mammalian species.

In one particularly preferred embodiment,
  a. the analyte comprises human chorionic gonadotropin (hCG);
  b. the labeled binding reagent comprises a monoclonal mouse anti-human chorionic gonadotropin antibody;
  c. the capture control reagent comprises a non-human, non-murid mammalian anti-mouse antibody; and
  d. the presence of human chorionic gonadotropin in the liquid sample is a marker of the physiological condition of pregnancy.

In another aspect, the invention provides a device for detecting the possible presence of an analyte in a liquid sample, wherein the device comprises:
  a. the test strip described above;
  b. a housing containing the test strip, wherein the housing comprises at least one opening to expose the surface of the test strip in the application zone for application of the liquid sample.

Preferably, the housing further comprises an opening to expose the surface of the test strip in the capture test zone and capture control zone for detection of test results. More preferably, the housing comprises indicia identifying the sample application zone, the capture test zone, and the capture control zone.

In another aspect, the present invention provides a test strip for detecting the possible presence of an analyte in a liquid sample applied to the test strip, the test strip comprising a dry porous medium comprising a single hydrophilic matrix, wherein the single hydrophilic matrix comprises:

a. a monolithic hydrophilic matrix comprising a network of fibers; and
b. a series of zones comprising:
  i. a sample application zone;
  ii. a conjugate release zone comprising a labeled binding reagent, wherein
    (a) the labeled binding reagent comprises:
      (i) a label;
      (ii) a solid substrate comprising a carrier bead, wherein the carrier bead is mobile within the matrix when the carrier bead and matrix are wet; and
      (iii) a ligand that specifically binds to the analyte to form a first complex comprising the labeled binding reagent and the analyte; and
    (b) the labeled binding reagent is dry on the test strip prior to application of the liquid sample and is released into mobile form upon contact with the liquid sample;
  iii. a capture test zone comprising a capture test reagent, wherein:
    (a) the capture test reagent comprises:
      (i) a solid substrate comprising a capture test bead; and
      (ii) a ligand that specifically binds to the analyte or to the first complex to form a second complex comprising the labeled binding reagent, the analyte, and the capture reagent; and
    (b) the capture test reagent is dry on the test strip prior to application of the liquid sample and is substantially immobile;
  iv. a capture control zone comprising a capture control reagent, wherein
    (a) the capture control reagent comprises:
      (i) a solid substrate comprising a capture control bead; and
      (ii) a ligand that specifically binds to the labeled binding reagent to form a third complex comprising the labeled binding reagent and the capture control reagent; and
    (b) the capture control reagent is dry on the test strip prior to application of the liquid sample and is substantially immobile; and
  v. an absorbent zone, wherein the absorbent zone draws the liquid sample through the dry porous medium of the test strip by capillary action.

In still another aspect, the present invention provides a method for making a test strip for detecting the possible presence of an analyte in a liquid sample applied to the test strip, the test strip comprising a dry porous medium comprising a single hydrophilic matrix comprising a monolithic hydrophilic matrix, wherein the method comprises:
a. providing a monolithic hydrophilic matrix, wherein the monolithic hydrophilic matrix comprises a network of fibers;
b. creating a conjugate release zone on the monolithic hydrophilic matrix by:
  i. providing a labeled binding reagent, wherein the labeled binding reagent comprises:
    a label;
    a solid substrate comprising a carrier bead, wherein the carrier bead is mobile within the matrix when the carrier bead and matrix are wet; and
    a ligand that specifically binds to the analyte to form a first complex comprising the labeled binding reagent and the analyte; and
  ii. suspending the labeled binding reagent in a buffer;
  iii. applying the labeled binding reagent suspension to a first zone of the monolithic hydrophilic matrix;
c. creating a capture test zone on the monolithic hydrophilic matrix by:
  i. providing a capture test reagent, wherein the capture test reagent comprises:
    a solid substrate comprising a capture test bead;
    a ligand that specifically binds to the analyte or to the first complex to form a second complex comprising the labeled binding reagent, the analyte, and the capture test reagent; and
  ii. suspending the capture test reagent in a buffer;
  iii. applying the capture test reagent suspension to a second zone of the monolithic hydrophilic matrix, wherein the second zone is downstream from the first zone; and
d. creating a capture control zone on the monolithic hydrophilic matrix by:
  i. providing a capture control reagent, wherein the capture control reagent comprises:
    a solid substrate comprising a capture control bead; and
    a ligand that binds to the labeled binding reagent to form a third complex comprising the labeled binding reagent and the capture control reagent; and
  ii. suspending the capture control reagent in a buffer;
  iii. applying the capture control reagent suspension to a third zone of the monolithic hydrophilic matrix, wherein the third zone is downstream from the second zone; and
e. drying the monolithic hydrophilic matrix to yield a dry porous medium.

In yet another aspect, the present invention provides a method of using a test strip to detect the possible presence of an analyte in a liquid sample applied to the test strip, wherein the method comprises:
a. providing a test strip comprising a dry porous medium comprising a single hydrophilic matrix, wherein the single hydrophilic matrix comprises:
  i. a monolithic hydrophilic matrix comprising a network of fibers; and
  ii. a series of zones comprising:
    (a) a sample application zone;
    (b) a conjugate release zone comprising a labeled binding reagent, wherein
      (i) the labeled binding reagent comprises:
        a label;
        a solid substrate comprising a carrier bead, wherein the carrier bead is mobile within the matrix when the carrier bead and matrix are wet; and
        a ligand that specifically binds to the analyte to form a first complex comprising the labeled binding reagent and the analyte; and
      (ii) the labeled binding reagent is dry on the test strip prior to application of the liquid sample and is released into mobile form upon contact with the liquid sample;
    (c) a capture test zone comprising a capture test reagent, wherein
      (i) the capture test reagent comprises:
        a solid substrate comprising a capture test bead; and
        a ligand that specifically binds to the analyte or to the first complex to form a second complex comprising the labeled binding reagent, the analyte, and the capture reagent; and
  (ii) the capture test reagent is dry on the test strip prior to application of the liquid sample and is substantially immobile;
(d) a capture control zone comprising a capture control reagent, wherein
  (i) the capture control reagent comprises:
    a solid substrate comprising a capture control bead; and
    a ligand that specifically binds to the labeled binding reagent to form a third complex comprising the labeled binding reagent and the capture control reagent; and
  (ii) the capture control reagent is dry on the test strip prior to application of the liquid sample and is substantially immobile; and
(e) an absorbent zone, wherein the absorbent zone draws the liquid sample through the dry porous medium of the test strip by capillary action;
b. obtaining a liquid sample;
c. applying the liquid sample to the sample application zone of the test strip;
d. wicking the liquid sample through single hydrophilic matrix to the conjugate release zone;
e. contacting the labeled binding reagent with the liquid sample to mobilize the labeled binding reagent and to permit formation of the first complex if the liquid sample comprises analyte;
f. wicking the liquid sample and the labeled binding reagent, whether alone or in the first complex, through the single hydrophilic matrix to the capture test zone;
g. contacting the capture test reagent with the liquid sample and the labeled binding reagent, whether alone or in the first complex, to permit formation of the second complex if the first complex is present;
h. concentrating the second complex in the network of fibers in the capture test zone of the single hydrophilic matrix;
i. detecting the presence of the second complex in the capture test zone;
j. wicking the liquid sample and the labeled binding reagent through the single hydrophilic matrix to the capture control zone;
k. contacting the capture control reagent with the liquid sample and the labeled binding reagent to permit formation of the third complex;
l. concentrating the third complex in the network of fibers in the capture control zone of the single hydrophilic matrix; and
m. detecting the presence of the third complex in the capture control zone.

In yet another aspect, the present invention provides a method of diagnosing a disease, a phenotype, a genotype, or a physiological condition in an organism by detecting the presence of an analyte associated with the disease, the phenotype, the genotype, or the physiological condition in a liquid biological sample, wherein the method comprises:
  a. providing a test strip comprising a dry porous medium comprising a single hydrophilic matrix, wherein the single hydrophilic matrix comprises:
    i. a monolithic hydrophilic matrix comprising a network of fibers; and
    ii. a series of zones comprising:
      (a) a sample application zone;
      (b) a conjugate release zone comprising a labeled binding reagent, wherein
        (i) the labeled binding reagent comprises
          a label;
          a solid substrate comprising a carrier bead, wherein the carrier bead is mobile within the matrix when the carrier bead and matrix are wet; and
          a ligand that specifically binds to the analyte to form a first complex comprising the labeled binding reagent and the analyte; and
        (ii) the labeled binding reagent is dry on the test strip prior to application of the liquid sample and is released into mobile form upon contact with the liquid sample;
      (c) a capture test zone comprising a capture test reagent, wherein
        (i) the capture test reagent comprises:
          a solid substrate comprising a capture test bead; and
          a ligand that specifically binds to the analyte or to the first complex to form a second complex comprising the labeled binding reagent, the analyte, and the capture reagent; and
        (ii) the capture test reagent is dry on the test strip prior to application of the liquid sample and is substantially immobile;
      (d) a capture control zone comprising a capture control reagent, wherein
        (i) the capture control reagent comprises:
          a solid substrate comprising a capture control bead; and
          a ligand that specifically binds to the labeled binding reagent to form a third complex comprising the labeled binding reagent and the capture control reagent; and
        (ii) the capture control reagent is dry on the test strip prior to application of the liquid sample and is substantially immobile; and
      (e) an absorbent zone, wherein the absorbent zone draws the liquid sample through the dry porous medium of the test strip by capillary action;
b. obtaining a liquid biological sample from an organism;
c. applying the liquid biological sample to the sample application zone of the test strip;
d. wicking the liquid biological sample through single hydrophilic matrix to the conjugate release zone;
e. contacting the labeled binding reagent with the liquid biological sample to mobilize the labeled binding reagent and to permit formation of the first complex;
f. wicking the liquid biological sample, the labeled binding reagent, and the first complex through the single hydrophilic matrix to the capture test zone;
g. contacting the capture test reagent with the liquid biological sample, the labeled binding reagent, and the first complex to permit formation of the second complex;
h. concentrating the second complex in the network of fibers in the capture test zone of the single hydrophilic matrix;
i. detecting the presence of the second complex in the capture test zone;
j. wicking the liquid sample and the labeled binding reagent through the single hydrophilic matrix to the capture control zone;
k. contacting the capture control reagent with the liquid sample and the labeled binding reagent to permit formation of the third complex;

l. concentrating the third complex in the network of fibers in the capture control zone of the single hydrophilic matrix;

m. detecting the presence of the third complex in the capture control zone; and n. diagnosing the disease, the phenotype, the genotype, or the physiological condition of the organism.

In another aspect, the present invention provides a test strip for detecting the possible presence of any one of multiple analytes in a liquid sample applied to the test strip, the test strip comprising a dry porous medium comprising a single hydrophilic matrix, wherein the single hydrophilic matrix comprises:

a. a monolithic hydrophilic matrix comprising a network of fibers; and b. a series of zones comprising:
  i. a sample application zone;
  ii. a conjugate release zone comprising a plurality of labeled binding reagents, wherein
    (a) each labeled binding reagent comprises:
      (i) a label;
      (ii) a solid substrate comprising a carrier bead, wherein the carrier bead is mobile within the matrix when the carrier bead and matrix are wet; and
      (iii) a ligand that specifically binds to one of the analytes to form a first complex comprising the labeled binding reagent and the analyte;
    (b) each labeled binding reagent is dry on the test strip prior to application of the liquid sample and is released into mobile form upon contact with the liquid sample; and
    (c) each labeled binding reagent specifically binds to a different analyte among the multiple analytes of the test;
  iii. a capture test zone comprising a plurality of capture test reagents, wherein:
    (a) each capture test reagent comprises:
      (i) a solid substrate comprising a capture test bead; and
      (ii) a ligand that specifically binds to one of the analytes or to one of the first complexes to form a second complex comprising the labeled binding reagent, analyte, and the capture reagent;
    (b) each capture test reagent is dry on the test strip prior to application of the liquid sample and is substantially immobile; and
    (c) each capture test reagent specifically binds to a different analyte or first complex among the multiple analytes and first complexes of the test;
  iv. a capture control zone comprising at least one capture control reagent, wherein
    (a) the capture control reagent comprises:
      (i) a solid substrate comprising a capture control bead; and
      (ii) a ligand that specifically binds to the labeled binding reagent to form a third complex comprising the labeled binding reagent and the capture control reagent; and
    (b) the capture control reagent is dry on the test strip prior to application of the liquid sample and is substantially immobile; and
  v. an absorbent zone, wherein the absorbent zone draws the liquid sample through the dry porous medium of the test strip by capillary action.

In yet another aspect, the present invention provides a method of diagnosing a disease, a phenotype, the genotype, or a physiological condition in an organism by detecting the presence of at least one analyte associated with the disease, the phenotype, the genotype, or the physiological condition in a liquid biological sample, wherein the method comprises:

a. providing the test strip above capable of detecting the presence of any one of multiple analytes;

b. obtaining a liquid biological sample from an organism;

c. applying the liquid biological sample to the sample application zone of the test strip;

d. wicking the liquid biological sample through the single hydrophilic matrix to the conjugate release zone;

e. contacting the labeled binding reagents with the liquid biological sample to mobilize the labeled binding reagents and to permit formation of at least one first complex;

f. wicking the liquid biological sample, the labeled binding reagents, and the one or more first complexes through the single hydrophilic matrix to the capture test zone;

g. contacting the capture test reagents with the liquid biological sample, the labeled binding reagents, and the one or more first complexes to permit formation of at least one second complex;

h. concentrating the one or more second complexes in the network of fibers in the capture test zone of the single hydrophilic matrix;

i. detecting the presence of the second complexes in the capture test zone;

j. wicking the liquid sample and the labeled binding reagents through the single hydrophilic matrix to the capture control zone;

k. contacting the capture control reagents with the liquid sample and the labeled binding reagents to permit formation of at least one third complex;

l. concentrating the third complexes in the network of fibers in the capture control zone of the single hydrophilic matrix;

m. detecting the presence of the third complexes in the capture control zone; and n. diagnosing the disease, the phenotype, the genotype, or the physiological condition of the organism.

In one embodiment, more than one disease, phenotype, genotype, or physiological condition can be diagnosed simultaneously, preferably, wherein each analyte is used to diagnose a different disease, phenotype, genotype, or physiological condition, including, but not limited to, a disease, phenotype, genotype, or physiological condition selected from the group consisting of the following: pregnancy, cancer, heart disease, hypertension, elevated cholesterol level, hyperglycemia, hypoglycemia, diabetes, malaria, tuberculosis, acquired immune deficiency syndrome (AIDS), a sexually transmitted disease (e.g., syphilis, gonorrhea, herpes), dengue fever, Ebola, Lassa fever, hepatitis, pneumonia (e.g., bacterial, viral), and a genetic disease.

In one embodiment, the method tests for the presence of each of the following pathogens:

a. human immunodeficiency virus;

b. tuberculosis; and c. malaria.

In another aspect, the invention provides a method of separating components in a blood sample, wherein the method comprises:
- a. providing the test strip above capable of detecting the presence of any one of multiple analytes, wherein the test strip detects at least one of the following:
  - i. protein;
  - ii. immunoglobulin (IgG);
  - iii. cholesterol;
- b. obtaining a blood sample;
- c. applying the blood sample to the sample application zone of the test strip;
- d. wicking the blood sample through the single hydrophilic matrix to the conjugate release zone;
- e. contacting the labeled binding reagents with the blood sample to mobilize the labeled binding reagents and to permit formation of at least one first complex;
- f. wicking the blood sample, the labeled binding reagents, and the one or more first complexes through the single hydrophilic matrix to the capture test zone;
- g. contacting the capture test reagents with the blood sample, the labeled binding reagents, and the one or more first complexes to permit formation of at least one second complex;
- h. concentrating the one or more second complexes in the network of fibers in the capture test zone of the single hydrophilic matrix;
- i. detecting the presence of the second complexes in the capture test zone;
- j. wicking the blood sample and the labeled binding reagents through the single hydrophilic matrix to the capture control zone;
- k. contacting the capture control reagents with the liquid sample and the labeled binding reagents to permit formation of at least one third complex;
- l. concentrating the third complexes in the network of fibers in the capture control zone of the single hydrophilic matrix;
- m. detecting the presence of the third complexes in the capture control zone; and
- n. removing plasma from the strip.

In another aspect, the present invention provides a test strip for a competitive assay for detecting the possible presence of an analyte in a liquid sample applied to the test strip, the test strip comprising a dry porous medium comprising a single hydrophilic matrix, wherein the single hydrophilic matrix comprises:
- a. a monolithic hydrophilic matrix comprising a network of fibers; and
- b. a series of zones comprising:
  - i. a sample application zone;
  - ii. a conjugate release zone comprising a labeled binding reagent, wherein
    - (a) the labeled binding reagent comprises:
      - (i) a label;
      - (ii) a solid substrate comprising a carrier bead, wherein the carrier bead is mobile within the matrix when the carrier bead and matrix are wet; and
      - (iii) a ligand that specifically binds to the analyte to form a first complex comprising the labeled binding reagent and the analyte; and
    - (b) the labeled binding reagent is dry on the test strip prior to application of the liquid sample and is released into mobile form upon contact with the liquid sample;
  - iii. a capture test zone comprising a capture test reagent, wherein:
    - (a) the capture test reagent comprises:
      - (i) a solid substrate comprising a capture test bead; and
      - (ii) a ligand comprising either the analyte or an analog of the analyte; and
    - (b) the capture test reagent is dry on the test strip prior to application of the liquid sample and is substantially immobile;
  - iv. a capture control zone comprising a capture control reagent, wherein
    - (a) the capture control reagent comprises:
      - (i) a solid substrate comprising a capture control bead; and
      - (ii) a ligand that specifically binds to the labeled binding reagent to form a second complex comprising the labeled binding reagent and the capture control reagent; and
    - (b) the capture control reagent is dry on the test strip prior to application of the liquid sample and is substantially immobile; and
  - v. an absorbent zone, wherein the absorbent zone draws the liquid sample through the dry porous medium of the test strip by capillary action.

The present invention also provides methods for concentrating the indicator.

In another aspect, the present invention provides a method for concentrating a reagent in a porous medium comprising a monolithic hydrophilic matrix, wherein the method comprises:
- a. providing a monolithic hydrophilic matrix;
- providing a reagent, wherein the reagent comprises:
  - i. a solid substrate; and
  - ii. an agglutinating agent activated upon contact with an aqueous liquid;
- b. suspending the reagent in a buffer to yield a reagent suspension;
- c. applying the reagent suspension to the monolithic hydrophilic matrix;
- d. drying the reagent suspension on the monolithic hydrophilic matrix; and
- e. applying an aqueous liquid to the porous medium to activate the agglutinating agent in order to self-agglutinate the solid substrate of the reagent for concentrating the reagent in the monolithic hydrophilic matrix of the porous medium.

Preferably, the monolithic hydrophilic matrix comprises a network of fibers, the solid substrate of the reagent comprises a bead, and the agglutinating agent comprises polyethylene glycol (PEG).

In yet another aspect, the present invention provides a method for concentrating a reagent in a porous medium comprising a monolithic hydrophilic matrix, wherein the method comprises:
- a. providing a monolithic hydrophilic matrix;
- b providing a reagent, wherein the reagent comprises:
  - i. a negatively-charged solid substrate;
  - ii. a positively-charged ligand attached to the solid substrate;
- c. suspending the reagent in a buffer to yield a reagent suspension;
- d. applying the reagent suspension to the monolithic hydrophilic matrix;
- e. drying the reagent suspension on the monolithic hydrophilic matrix;

f. contacting the ligand with an aqueous liquid having a pH below the pI of the ligand and comprising a substance to which the ligand binds; and g. altering the overall charge of the reagent in order to self-agglutinate the reagent for concentrating the reagent in the monolithic hydrophilic matrix of the porous medium.

Preferably, the monolithic hydrophilic matrix comprises a network of fibers, the negatively-charged solid substrate of the reagent comprises a bead, the positively-charged ligand comprises a protein. More preferably, the protein comprises an antibody or an antigen.

In one aspect, the present invention provides a single lateral flow function layer. In preferred embodiments, the layer comprises a matrix, more preferably a monolithic matrix, of glass fiber, non-woven polymer, or a combination thereof.

In one preferred embodiment, the present invention provides a single lateral flow function layer comprising a mixture of polymer and glass fiber, which can act as a suitable matrix. This mixture had previously been shown to work as a blood separator and conjugate release, as well as a sample pad and absorbent. With the greatest surprise, however, the teaching of the present invention shows that the same material can be used as a reaction matrix in a single-layer lateral flow function format.

The hydrophilic composite is low protein binding, and the capture reagents will not normally bind very well. However if the capture reagents are initially immobilized on a carrier particle (such as a latex bead) whose diameter is between 40 and 70% of the nominal pore size (or greater than the size for which there is a 98% absorption efficiency but small enough to enter the matrix) the latex beads will be efficiently retained within the matrix. The sensitivity of the test will depend upon the numbers of carrier beads added, their surface area (related to bead diameter) and the amount of capture reagent immobilized on their surface. The system can be further improved by the use of an agglutinating agent, such as polyethylene glycol, on the capture beads (both test and control) or by use of a positively-charged ligand on a negatively-charged capture bead, as described infra.

The use of this type of this material has a number of advantages:

1) The composite is naturally hydrophilic and therefore does not require blocking (unlike membranes);
2) The composite is low protein so the background signal is low and therefore lowest detectable signal is reduced
3) In membranes as the wicking area increases (related to pore size) the available membrane surface area (and hence test sensitivity) is reduced. The composite signal is related to the surface area of the beads, not the composite. It would therefore be able to control the signal by varying the beads for the same pore size material.
4) Small antigens will not attach well to membranes, however they can be covalently linked to the beads. The composite can therefore be used for any test.
5) The wicking rate of the composite is much higher then membranes, test will therefore run more quickly (desired by many test developers)
6) The immobilization to beads will allow better control of linkage chemistry, resulting in increased test shelf life. Alternatively, other materials, which have longer shelf life, can be attached.

The type of material that could work could be any bound glass fiber, however good results have been seen with a latex-bound glass.

Thus, while a glass fiber or a mixture of polymer and glass fiber has been shown to work for one or more of the features in the past, only now has it been demonstrated that the same material can function for all five areas at the same time. This finding is novel, unexpected, and quite surprising.

FIG. 1A shows an exploded view of an embodiment of the present invention. A device (10) comprising the test strip (20) within an upper housing (30) and lower housing (32) is shown. In a preferred embodiment, the upper housing (30) has two apertures (34, 36), one of which (34) provides the user with access to the sample application zone of the test strip (20), while the other (36) enables the user to visualize or otherwise detect the test results in the capture test zone and capture control zone. More preferably, indicia (40, 42, 44) are provided on the upper housing (30) to indicate the positions of the sample application zone (e.g., S (40)), the capture test zone (e.g., T (42)), and the capture control zone (e.g., C (44)).

Figure 1B:
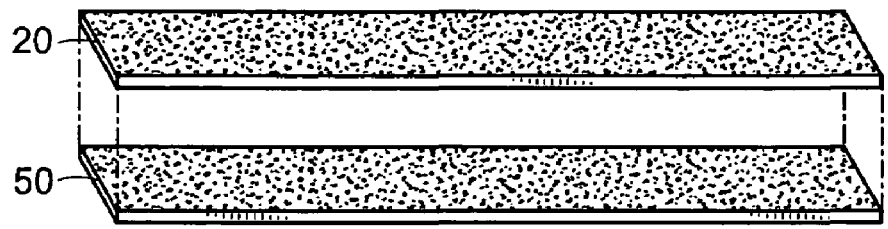
FIG. 1B depicts an exploded view of one embodiment of a single-layer lateral flow format test strip on a support strip.

As shown in FIGS. 1A and 1B, the test strip (20) may be additionally supported by a support strip (50), which may be made of plastic (e.g., polystyrene, PET, or vinyl) or some other appropriate material for support.

FIGS. 2A-2D depict a schematic top view of the test strip as it is being used. The test strip has a series of zones comprising a sample application zone (A), a conjugate release zone (B) comprising a labeled binding reagent (80), a capture test zone (C) comprising a capture test reagent (90), a capture control zone (D) comprising a capture control reagent (100), and an absorbent zone (E).

Figure 2A:
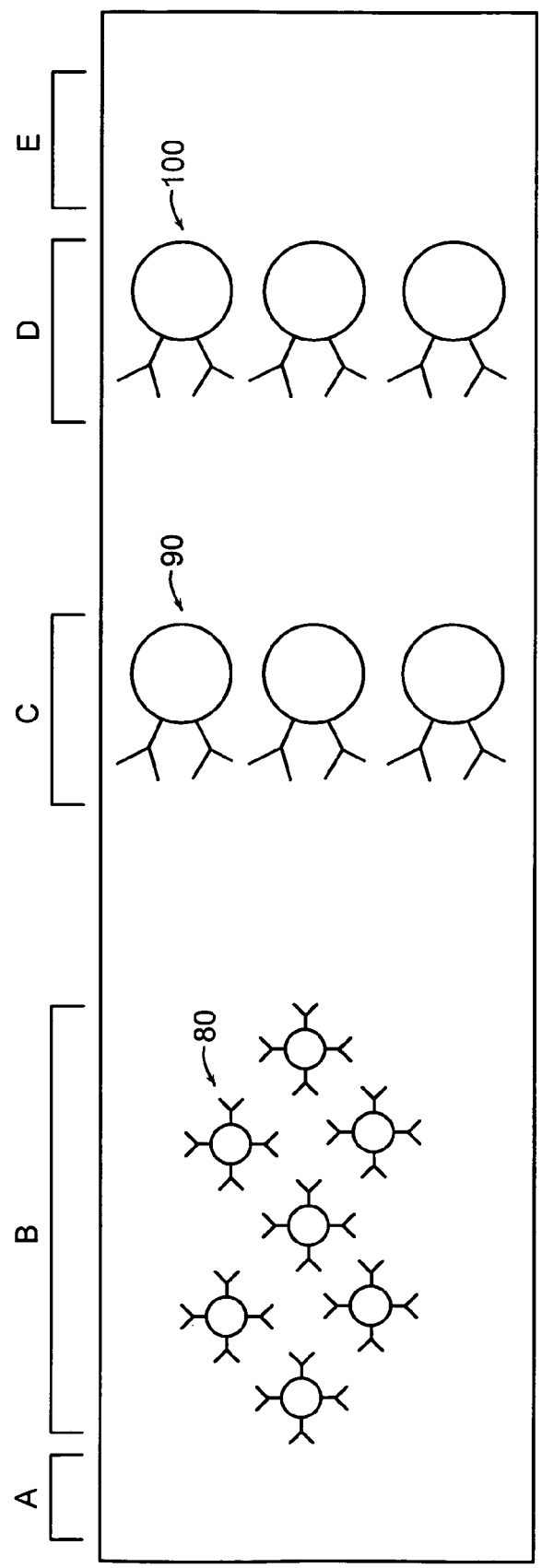
FIGS. 2A-2D depict a method of using a preferred embodiment of a single-layer lateral flow format.

The embodiment depicted in FIG. 2A shows a labeled binding reagent (80) comprising a carrier bead and an antibody ligand, a capture test reagent (90) comprising a capture bead and an antibody ligand, and a capture control reagent (100) comprising a capture bead and an antibody ligand.

Figure 2B:
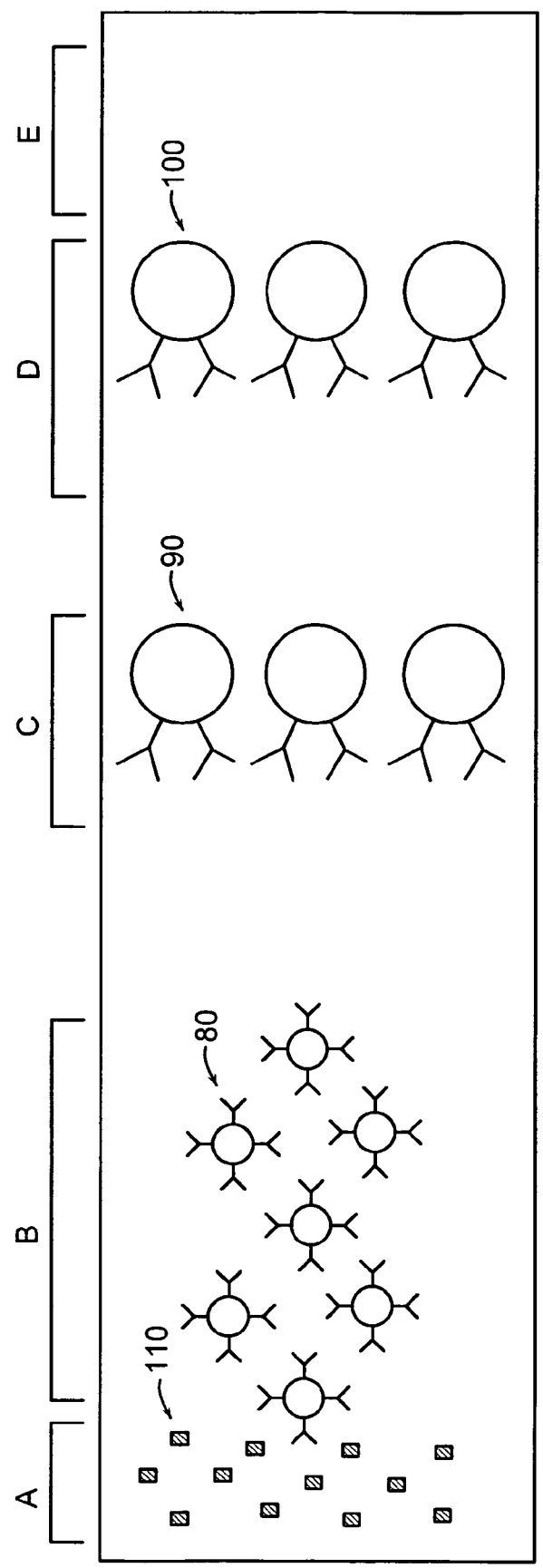
Figure 2C:
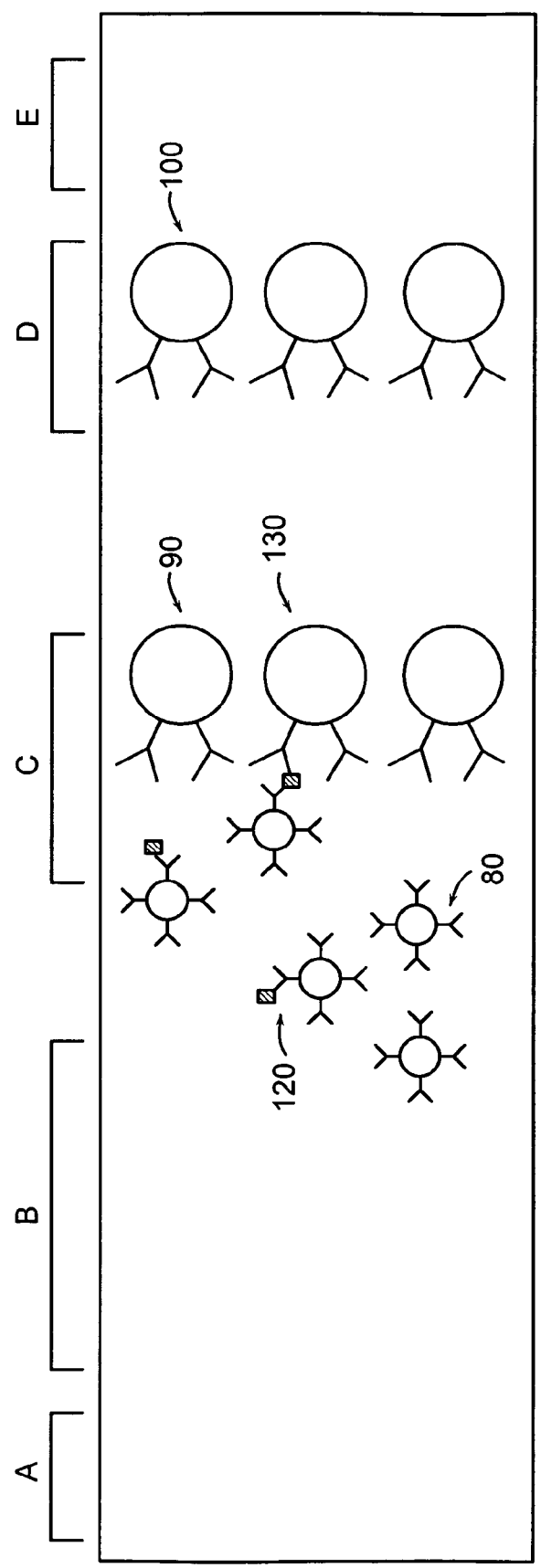

In FIG. 2B, a sample comprising an analyte (110) is applied to the sample application zone (A), and it is wicked via capillary action through the test strip to the conjugate release zone (B), where it will bind to some of the labeled binding reagent (80) to form the first complex (120), which comprises analyte (110) and labeled binding reagent (80) (see also FIG. 2C).

In FIG. 2C, the first complex (120) and some unbound labeled binding reagent (80) are wicked through the test strip to the capture test zone (C), where they contact the capture test reagent (90). In this example, the capture test reagent (90) also recognizes the analyte (110) and, therefore, binds the first complex (120) to form the second complex (130). The second complex (130) is largely immobilized in the matrix of the test strip and forms a line indicating a positive test result. "Largely immobilized" means that the capture test beads (90) may be jostled, may rotate, or may agglutinate, but they do not flow through the matrix as the labeled binding reagent of the conjugate release zone does. The capture test reagent (90) does not recognize the unbound labeled binding reagent (80).

Figure 2D:
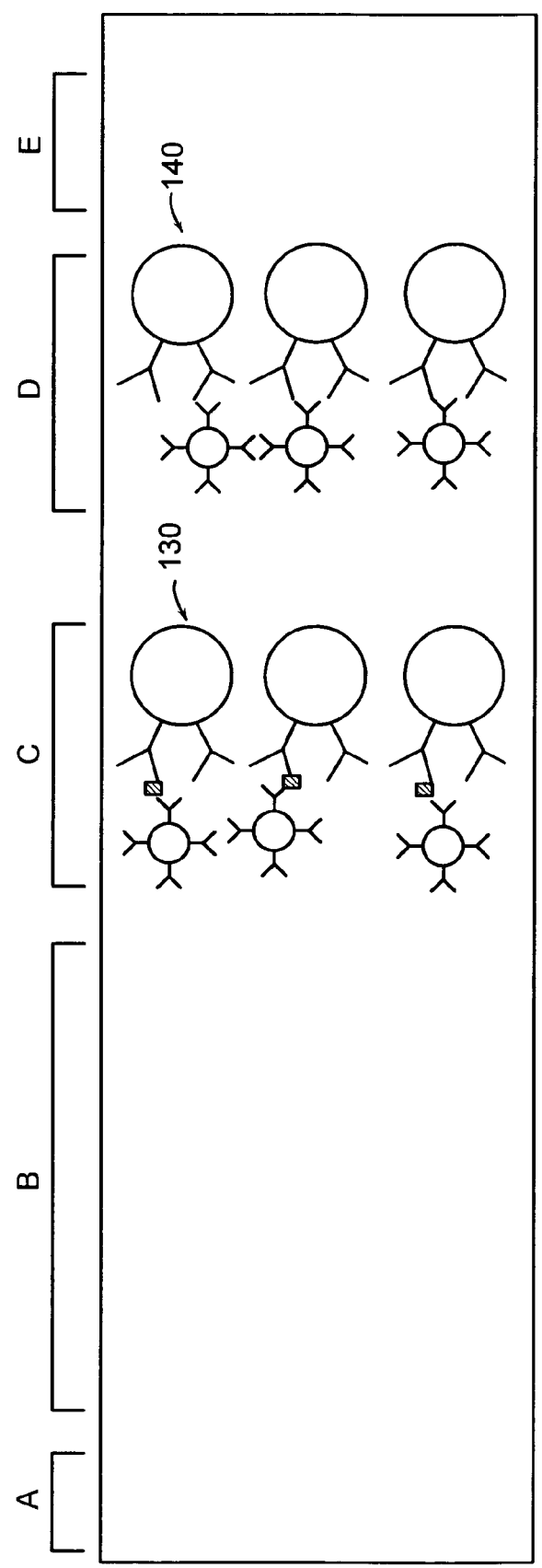

In FIG. 2D, the unbound labeled binding reagent (80) continues to wick through the test strip to the capture control zone (D), where it contacts the capture control reagent (100). In this example, the capture control reagent (100) recognizes and binds to the unbound antibody on the unbound labeled binding reagent (80) and finds to it to form the third complex (140). The third complex (140) is largely immobilized in the matrix of the test strip and forms a control line indicating that the wicking of the sample has reached the absorbent zone (E) and that test has worked. "Largely immobilized" means that, like the capture test beads (90), the capture control beads (100) may be jostled, may rotate, or may agglutinate, but they do not flow through the matrix as the labeled binding reagent of the conjugate release zone does.

In the test shown in FIGS. 2A-2D, a positive result has both a test line at the control test zone (C) and a control line at the capture control zone (D), while a negative result has only a control line at the capture control zone (D).

In one embodiment, there are multiple capture lines that each test for a separate analyte (along with the corresponding labeled binding reagents), enabling a sample to be tested for several analytes simultaneously.

This embodiment enables single sample to undergo multiple tests for a given disease, phenotype, genotype, or physiological condition. This type of testing capability is particularly useful, e.g., where the tests for a given disease, phenotype, genotype, or physiological condition have a high rate of false positives or false negatives.

Alternatively, a single sample can undergo tests for multiple diseases, phenotypes, genotypes, or physiological conditions. This type of testing capability is useful in a wide range of applications, including, but not limited to, routine screening in an annual medical physical; for medical testing in remote areas, where physician access to populations and/or patient access to physicians is limited (e.g., in rural areas both in the industrialized world and in developing nations); for large-scale testing settings, such as for epidemics or for large impoverished urban populations; for field work with patients; and for testing where only a limited quantity of sample material is available (e.g., for forensic purposes or for trauma patients and other patients who have lost significant amounts of blood or who have a reduced amount of blood or other bodily fluids). For example, in many parts of the world, there is a need for a simple method of testing for one or more of a number of diseases, particularly infectious diseases, in a rapid, low-cost, and efficient manner (with a device or materials that are easily transportable and less susceptible to degradation) in locations where there is little or no refrigeration, laboratory equipment, or transportation available. In regions or situations where multiple diseases commonly infect the same patient, a single sample could be tested for several diseases simultaneously. For example, it is envisioned that the present invention could be used to test infection with human immunodeficiency virus (HIV; associated with the development of acquired immune deficiency syndrome (AIDS)), tuberculosis, Ebola, malaria, Lassa fever, hepatitis (A, B, C, D, or E) and/or dengue fever. Alternatively, where a patient has a disease, such as a genetic hemoglobin disease, the present invention could test the genotype for sickle cell anemia and several types of thalassemias simultaneously.

In another embodiment, the test format is used to detect genetic mutations or polymorphisms.

In another embodiment, the test format comprises a competitive assay, where the binding reagent or one of the capture reagents is the same as (or an analog of) the analyte. This competitive assay format is particularly useful in tests for small analytes (such as drugs) where it would be difficult to form a "sandwich" assay due to steric problems.

In a preferred embodiment, the invention provides a single lateral flow function layer comprising a material that is low protein binding, has a fast wicking rate, and comprises a network of fibers. Preferably, the material is hydrophilic. More preferably, the material comprises a network of glass fibers or microfibers. Still more preferably, the material comprises a network of glass fibers in combination with a polymer. The network of glass or glass-polymer fibers is capable of retaining beads (e.g., latex, gold) to which the conjugate is attached or beads (e.g., latex) for use as capture test reagents or as capture control reagents. Other substances include cast or moulded cellulose acetate and fused polyethylene. The size of the pores (e.g., between a network of fibers) depends on the size and purpose (i.e., conjugation vs. capture) of the beads and also depends on the nature of the sample and whether any separation or filtration is desired. If removal of erythrocytes (red blood cells) is desired, the material would have to have a pore size that retains red blood cells (a 98% retention efficiency—below about 3.5 microns); however if removal of red cells is not desired, the pore size could be larger. The larger the pore size, the larger the size of the bead needed to become entrapped. However, as the size of the bead increases, the available surface area for protein immobilization is reduced, resulting in decreased sensitivity.

Materials less suitable for the present invention include cellulose and nitrocellulose. Cellulose would not allow the sample to flow through the material quickly and would not allow the conjugate to release. It also does not function well as a blood separator in embodiments requiring blood separation. A nitrocellulose membrane is protein binding and tends towards hydrophobicity. The material would need to be blocked to make it work. The pore size needed for blood separation would be small and therefore test time would be too high. Also, nitrocellulose does not have the correct absorbency properties to act as a sample wick and absorbent. Time to flow along the material increases exponentially as the wicking distance increases. For example, flow for 0.5 cm takes 5 seconds, flow for 1 cm takes 15 seconds, flow for 1.5 cm takes 30 seconds, flow for 2 cm takes 90 seconds, etc. Moreover, it would not function well as a wick for large volumes of samples. While it can work for low volumes (e.g., <30 microliters) however it would not work for larger volumes. For a strip comprising only nitrocellulose, the length of material required would be approximately 6-8 cm, and test time would be quite lengthy. At this rate, there would be a danger of the sample drying before wicking the length of the test strip. For test results comparing the wicking rate of three nitrocellulose membranes with that of an embodiment of the present invention, see Example 2 and FIG. 4.

Nonetheless, nitrocellulose and cellulose materials, such as cellulose acetate, may still be useful in some embodiments of the invention. Foams, including wholly or partially open-celled foams, and particulates, including immobilized particulates may also be useful in the present invention.

In addition to glass fiber, either alone or in combination with polymers and non-woven plastics, basically any hydrophilic material with the correct pore size (e.g., hydrophilic membranes, such as polyester sulfone (PES), polyvinylidene fluoride (PVDF), fused polyethylene (PE), non-woven materials, and moulded cellulose acetate). If the pore size is too large (e.g., polypropylene mesh), the membrane would not function as there would not be efficient particle trapping. As a result, many materials, which are known in the art to be successful for conjugate release, would not necessarily function well in the present invention.

In a more preferred embodiment, the present invention provides a single-layer lateral flow format comprising a polymer-glass fiber matrix, which is naturally hydrophilic, substantially non-protein binding, and fast flowing, which has high sensitivity and a low background and is simple to manufacture. More preferably, the polymer-glass fiber matrix comprises a latex-bound (e.g., polystyrene (PS) or polymethylmethacrylate (PMMA)) glass fiber matrix. In this embodiment, the matrix serves simultaneously as a sample wick, a filter/separator (e.g., a blood separator), a conjugate release pad, a reaction membrane, and an absorbent. (An additional absorbant pad may be added, but is not necessary.) Preferably, the degree of natural hydrophilicity obviates any need for blocking. In a more preferred embodiment, the material comprises a Whatman SLF5™ single-layer lateral flow format comprising a Whatman FUSION 5™ matrix, a latex-bound glass fiber, having the properties shown in Table 1.

TABLE 1

| KEY PROPERTY | SPECIFICATION | |
| --- | --- | --- |
| | IDEAL | RANGE |
| Grammage, gsm | 75 | 65-85 |
| Thickness, µm @ 53 kPa | 370 | Max 400 |
| Gurley sec/100 ml/01.1 sq in | 16 | 14-22 |
| M/D Tensile, N/15 mm | | Min 15 |
| M/D Wet Tensile, N/15 mm | | Min 5 |
| Pressure Drop, mm $H_2O$ @ 10.5 fpm | 16 | 13-18 |
| Mean pore size, µm | 5.1 | 4.6-5.6 |

A conjugate in an appropriate buffer is striped onto the test strip. The nature of the conjugate will depend on the nature of the test being performed and is discussed more fully, infra.

In a preferred embodiment, the ligand is attached to carrier beads to form the conjugate. The carrier beads used as labeled binding reagents must be retained within the structure of the network (e.g., via physical sorption), but must be capable of being released into mobile form upon contact with the liquid sample. The beads are preferably gold and should be capable of protein or nucleotide binding. Alternatively, the beads may be latex, selenium, or other suitable materials. The binding reagent (e.g., an antibody or oligonucleotide) is immobilized to the carrier beads, which are striped (as a colloidal mixture in an appropriate buffer) onto the lateral flow test strip. (Alternatively, the mixture may be dotted or may take any other shape appropriate to the use of a single-layer lateral flow format.) Generally, however, the detection beads do not have to have any particular shape; rather, the shape of the bead application is primarily relevant to the capture line(s). In one preferred embodiment, the carrier bead comprises a 40-80 nm gold bead. In another preferred embodiment, the carrier bead comprises a 100-800 nm latex bead.

The capture beads used as capture test reagents and capture control reagents must be retained within the structure of the network (e.g., via physical entrapment) and must remain substantially immobile during use of the lateral flow test strip, even when contacted with the liquid sample. The beads are preferably latex, but may be any material that does not interfere with the label on the carrier beads, that is, without any inherent color or without a color that will show up against the strip itself. Other potential materials include silica, glass, alumina, cellulose, or sugar (e.g., dextrose, etc.). Ideally, the capture beads form a tight formation so that the label on the carrier beads captured by the capture beads is easily readable. The capture test reagent or capture control reagent (e.g., an antibody or oligonucleotide) is immobilized to the capture test beads or capture control beads, respectively, which are striped (as colloidal mixtures in an appropriate buffer) onto the lateral flow test strip. (Alternatively, the mixture may be dotted or may take any other shape, such as a plus or X-shape or any other shape appropriate to the use of a single-layer lateral flow format.)

In a preferred embodiment, the latex beads (e.g., PMMA, PS, etc.) comprise sulfate terminated beads. These materials bind proteins due to physical binding (charge and hydrophobicity). Alternatively, a covalent binding latex bead may be used. Examples of preferred embodiments include latex beads manufactured by Estapor Microspheres or Bangs Laboratories, Inc. The bead size must be small enough to enter the material, but large enough to become trapped. For FUSION 5™ (Whatman), the optimal bead size is approximately 2 microns; the FUSION 5™ material has a 98% retention efficiency for beads of approximately 2.5 microns. Beads of 2.5 microns would not generally enter the matrix, whereas beads of below 1.5 microns would be washed out of the matrix.

A typical protocol for applying the beads would be as follows: At the conjugate release zone apply 40 nm gold colloid that has been conjugated to monoclonal anti-beta hCG (labeled binding reagent), concentrated or $OD_{520}$=10. Antibodies are often mouse monoclonal antibodies. Apply to the FUSION 5™ from a borate buffer pH 8.2 containing 1% Tween 20, 0.5% PVA and 0.2% BSA. At the capture zone (capture test zone and capture control zone, respectively) apply two separate lines, one being a 2 micron latex bead conjugated to anti-alpha hCG (capture test reagent), the second being a 2 micron latex bead conjugated to anti-mouse IgG (capture control reagent). The control antibodies are often anti-mouse Ab (e.g., goat anti-mouse) on and sometimes something that sticks to gold. Dry the test. After drying apply the sample. While in some embodiments, 100 µl aliquots of beads have been used, the amount of sample and the amounts of beads applied will vary considerably depending on the materials used.

In some embodiments, it may be possible for the capture control beads to bind to the first complex (e.g., the complex comprising the analyte and the labeled binding reagent), particularly if there is an excess of the first complex and if the binding by the capture control beads is less specific or is capable of taking place both in the presence, and in the absence, of the analyte. Because the test sample reaches the capture test zone first, the binding at the capture control zone will not affect the results of the test, and one purpose of the capture control zone is to demonstrate that the sample has flowed, or wicked, beyond the capture test zone to provide assurance that the result does not comprise a false negative test result. (The capture test reagent is carefully chosen for specificity in order to avoid a false positive test result.)

In a preferred embodiment, polyethylene glycol (PEG) is added to improve agglutination of beads. The amount of capture reagent is proportional to the surface area of the latex bead used. To improve sensitivity it would be necessary to increase the surface area; however this approach would entail using smaller beads, which would not stick to the matrix. To solve this problem, it is possible to use a smaller bead that agglutinates on drying. Self-agglutination of latex beads can be achieved either by including an agent to make the beads stick (e.g., PEG), by working at a pH below the pI of the protein on the bead surface, or by working at a high ionic strength (e.g., high salt concentration). The additive idea relies upon the fact that as the beads dry, water leaves the system. Therefore, if the original concentration of the additive will not cause agglutination, as the system dries, the effective concentration of the additive increases, until eventually the concentration reaches a critical point when the bead auto-agglutinates. The agglutinating agent is preferably PEG or some other hydrophilic agent or polymer, or it can be a reagent that adheres to the protein on the bead surface. With respect to the pH alteration, the charge repulsion of beads normally keeps them apart, but if the proteins on the bead surface attract other conjugates, the beads would stick together. Typically latex beads are negatively charged, therefore to make them attract, the proteins are positively charged by reducing the pH of the solution. Alternatively, the use of electrolytes (i.e., high salt concentration) could also cause agglutination of the beads. Where agglutinating agents or procedures are used, the size of the capture test beads and capture control beads may be decreased. Without wishing to be bound by theory, a lumpy conglomerate comprised of a clump of beads will have a higher surface area than a large bead. The presence of an increased concentration of salt will also cause agglutination due to the reduction of the zeta potential of the colloidal particles.

Preferably, the invention is used for the treatment of vertebrates; for the treatment of vertebrate cells, cell lines, tissues, or organs; for research purposes relating thereto; or for any other purposes encompassed by the description above. More preferably, the invention is used for the treatment of mammals; for the treatment of mammal cells, cell lines, tissues, or organs; for research purposes relating thereto; or for any other purposes encompassed by the description above. Still more preferably, the invention is used for the treatment of mammals; for the treatment of mammal cells, cell lines, tissues, or organs; for research purposes relating thereto; or for any other purposes encompassed by the description above.

The following definitions are provided for specific terms, which are used in the written description.

As used in the specification and claims, the singular form "a", "an" and "the" include plural references unless the context clearly dictates otherwise. For example, the term "a molecule" also includes a plurality of molecules.

As used herein, an "analyte" is the element of the sample to be detected by the test strip. The analyte specifically binds the labeled binding reagent in the conjugate release zone of the test strip. In some embodiments, the presence or absence of the analyte may be used to determine the physiological condition of an organism from which the sample was obtained. Alternatively, the presence or absence of the analyte may be used to detect, for example, contamination of a sample. A wide range of other uses will occur to one of skill in the art.

As used herein, a "porous medium" may have uniform or non-uniform pores. Alternatively, it may comprise, for example, a "matrix" or a "network of fibers" through which appropriately smaller sized materials can pass.

As used herein, the term "pore size" refers to the minimum size of particles that will be retained on or in the membrane. Thus, a membrane with a pore size of about 0.45 microns means that particles greater than about 0.45 microns will be retained on or in the membrane, those less than about 0.45 microns will pass through and will not be retained. In a network of fibers, the pore size is more variable than in a membrane or medium with regularly sized pores. The "average pore size" may be expressed as a range, and the "maximum pore size" and "minimum pore size" may vary considerably.

As used herein, "stably associated" with a substrate refers to an interaction between polymerized, crosslinked surface-modifying molecules and a substrate that remains intact after one or more washes in an aqueous solution and/or an organic solvent (such as an alcohol), and preferably, remains intact, after at least about 5, or at least about 10 washes. Preferably, a molecule which is "stably associated" with a substrate is one which remains attached to the substrate after exposure to at least about 90° C., for at least about 2 hours. "Stable associations" can be monitored by evaluating the wettability (i.e., hydrophilicity) of a substrate which is coated with difunctional surface-modifying molecules according to the invention.

As used herein, "hydrophilic" substance is one that absorbs or adsorbs water, while a "hydrophobic" substances is one that does not absorb or adsorb water.

As used herein, "wettable" refers to a membrane which is wetted across its entire surface without phobic patches.

As used herein, "a flow-through method" refers to a method where a solution is flowed through a substrate to coat the substrate with the solution.

As used herein, the term "functionally associated with" means that the coating is disposed, sorbed, or otherwise associated with the support and coating of the present invention such that the support and coating function together. That is, the coating can be adsorbed, absorbed, coated over, or otherwise disposed in functional relationship with the media.

The media can be combined with a "binder," which holds the fibers together. Some examples of binders well-known in the art are polyvinylacrylamide, polyvinylacrylate, polyvinylalcohol (PVA), polystyrene (PS), polymethylmethacrylate (PMMA), and gelatin.

As used herein, an "imprinted polymer" is a polymer composed into the fibrous matrix during its manufacture (e.g., a polymer put into a glass fiber matrix or other fiber matrix).

As used herein, a "monolithic hydrophilic matrix" is a hydrophilic matrix that is cast as a single piece. Alternatively, it is a hydrophilic matrix that is formed or composed of material without joints or seams, or a hydrophilic matrix consisting of or constituting a single unit.

As used herein, the "sample application zone" refers to the portion of the test strip to which the sample is applied.

As used herein, the "conjugate release zone" refers to the portion of the test strip initially comprising the "conjugate," such as a "labeled binding reagent," which recognizes the analyte when the analyte is present.

As used herein, the "capture zone" refers to the portion of the test strip comprising the "capture test zone" and the "capture control zone." The "capture test zone" refers to the portion of the test strip comprising the "capture test reagent," which recognizes either the analyte or the first complex comprising the analyte and the labeled binding reagent. The "capture control zone" refers to the portion of the test strip comprising the "capture control reagent," which recognizes the labeled binding reagent, either with or without the analyte.

As used herein, the "absorbent zone" refers to the portion of the test strip which draws the liquid sample through the test strip by wicking or capillary action.

As used herein, "specificity" refers to the ability of an antibody to discriminate between antigenic determinants. It also refers to the precise determinants recognized by a particular receptor or antibody. It also refers to the ability of a receptor to discriminate between substrates, such as drugs. With respect to nucleic acids, it refers to identity or complementarity as a function of competition or recognition/binding, respectively. "Specificity" of recognition or binding may be affected by the conditions under which the recognition or binding takes place (e.g., pH, temperature, salt concentration, and other factors known in the art).

As used herein, the term "largely immobile" or "largely immobilized" means that the substrate, such as a capture bead, may be jostled, may rotate, or may agglutinate, but does not flow or wick through the matrix.

As used herein, "agglutination" or "self-agglutination" refers to the clumping, clustering, agglomeration, or accumulation of moieties or substrates, including, but not limited to, beads.

As used herein, "wicking" is achieved by "capillary action," resulting from the "capillarity" of the sample on the test strip. "Capillarity" refers to the attraction between molecules, similar to surface tension, which results in the wetting of a solid by a liquid.

The "wicking rate" of a material can be measure as a function of wetting of a particular distance of the material over the course of a time period. The wicking rate depends on the nature of the material, the nature of the substance used for the wetting, and a variety of other conditions. The "wicking rates" of various materials can be compared.

As used herein, "line ramping" refers to the time taken for the rate of liquid flow through the striper to reach a constant rate after the start of the line application. It can be influenced by the rate of acceleration of the plunger in the applicator.

As used herein, a "ligand" is a molecule or molecular complex that can be bound by another molecule or molecular complex. The ligand may be, but is not limited to, a molecule or molecular complex bound by a receptor or a complementary fragment of nucleic acid.

As used herein, a "chimeric DNA" is at least two identifiable segments of DNA the segments being in an association not found in nature. Allelic variations or naturally occurring mutational events do not give rise to a chimeric DNA as defined herein.

As used herein, a "chimeric protein" or "fusion protein" is a protein with at least two identifiable segments, the segments being in an association not found in nature. In one embodiment, a chimeric protein may arise, for example, from expression of a chimeric DNA capable of being expressed as a protein and having at least two segments of DNA operably linked to enable expression of at least a portion of each segment as a single protein. Other embodiments will suggest themselves to one of ordinary skill in the pertinent art.

As used herein, the terms "polynucleotide" and "nucleic acid molecule" are used interchangeably to refer to polymeric forms of nucleotides of any length, which may have any three-dimensional structure, and may perform any function, known or unknown. The polynucleotides may contain deoxyribonucleotides (DNA), ribonucleotides (RNA), and/or their analogs, including, but not limited to, single-, double-stranded and triple helical molecules, a gene or gene fragment, exons, introns, messenger RNA (mRNA), transfer RNA (tRNA), ribosomal RNA (rRNA), small interfering RNA (siRNA), ribozymes, antisense molecules, complementary DNA (cDNA), genomic DNA (gDNA), recombinant polynucleotides, branched polynucleotides, aptamers, plasmids, vectors, isolated DNA of any sequence, isolated RNA of any sequence, nucleic acid probes, peptide nucleic acids (PNA), and primers. A nucleic acid molecule may also comprise modified nucleic acid molecules (e.g., comprising modified bases, sugars, and/or internucleotide linkers).

"Nucleic materials" and "materials from the nucleus" include the nuclear envelope and the contents of the nucleus, including genomic DNA (gDNA) or plasmid DNA. The "non-nucleic acid contents of the nucleus" include the components of the nuclear envelope and any other proteins or other substances of the nucleus that are not nucleic acids.

"Nucleic acids" include deoxyribonucleic acids (DNA) and ribonucleic acids (RNA) of various types, including genomic DNA (gDNA) and messenger RNA (mRNA) and derivatives thereof, such as modified DNA or RNA, including peptide nucleic acids (PNA). "Peptide nucleic acid" (PNA) is a polynucleotide analog in which the sugar-phosphate backbone is replaced by amide bonds. "Genetic material" comprises genomic DNA (gDNA), which is one type of DNA and encodes genetic information, or genetic RNA.

As used herein, a "genetic modification" refers to any addition, deletion or disruption to a cell's normal nucleotides. Any method which can achieve the genetic modification of antigen presenting cells (APC) are within the spirit and scope of this invention. Art recognized methods include viral mediated gene transfer, liposome mediated transfer, transformation, transfection and transduction.

As used herein, a "genetic mutation" is a genetic alteration and is a type of "genetic modification."

As used herein, a "polymorphism" or "genetic polymorphism" is a genetic variation and includes, but is not limited to, a single nucleotide polymorphism (SNP).

As used herein, a "genotype" is the genetic composition of an organism, and a "phenotype" is the physical appearance or characteristics of an organism.

A "peptide" is a compound of two or more subunit amino acids, amino acid analogs, or peptidomimetics. The subunits may be linked by peptide bonds or by other bonds (e.g., as esters, ethers, and the like).

An "amino acid" refers to either natural and/or unnatural or synthetic amino acids, including glycine and both D or L optical isomers, and amino acid analogs and peptidomimetics. "Amino acids" also includes imino acids. An "oligopeptide" refers to a short peptide chain of three or more amino acids. If the peptide chain is long (e.g., greater than about 10 amino acids), the peptide is a "polypeptide" or a "protein." While the term "protein" encompasses the term "polypeptide", a "polypeptide" may be a less than full-length protein.

A "tag peptide sequence" is a short peptide or polypeptide chain of 3 or more amino acids, which is attached to a protein of interest. In a preferred embodiment, a polypeptide, protein, or chimeric protein comprises a tag peptide sequence, which is used for purification, detection, or some other function, such as by specific binding to an antibody. The antibody may be in solution or bound to a surface (e.g., a bead, filter, or other material). The tag peptide sequence should not interfere with the function of the rest of the polypeptide, protein, or chimeric protein. An example of a tag peptide sequence useful in the present invention is a short c-Myc tag with six His residues fused at the carboxyl-terminus. Other examples will be well-known to those of ordinary skill in the pertinent art.

As used herein, "expression" refers to the process by which polynucleotides are transcribed into mRNA and/or translated into peptides, polypeptides, or proteins. If the polynucleotide is derived from genomic DNA, expression may include, but is not required to include, splicing of the mRNA transcribed from the genomic DNA, capping of the 5' end of the mRNA, polyadenylation of the 3' end of the mRNA, or other processing modifications or events.

As used herein, "signal sequence," or "secretory sequence" denotes the endoplasmic reticulum translocation sequence. This sequence encodes a "signal peptide," "secretory peptide," or "secretory domain" that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence may be excised by the cell during the maturation of a protein. Secretory sequences and domains of various species are well known in the art.

A "domain" is a region of a protein or polypeptide having a significant tertiary structure.

"Conservatively modified variants" of domain sequences also can be provided within the scope of the invention. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues. Alternatively, one or more amino acids may be substituted with an amino acid having a similar structure, activity, charge, or other property. Conservative substitution tables providing functionally similar amino acids are well-known in the art (see, e.g., *Proc. Natl. Acad. Sci. USA* 89: 10915-10919 (1992)).

The source of the nucleic acid or protein can be a biological sample containing whole cells. The whole cells can be, but are not restricted to, blood, bacterial culture, bacterial colonies, yeast cells, tissue culture cells, saliva, urine, drinking water, plasma, stool samples, semen, vaginal samples, sputum, plant cell samples, or various other sources of cells known in the scientific, medical, forensic, and other arts. The samples can be collected by various means known in the art, transported to the test strip, and then applied thereto.

A "host organism" is an organism or living entity, which may be prokaryotic or eukaryotic, unicellular or multicellular, and which is desired to be, or has been, a recipient of exogenous nucleic acid molecules, polynucleotides, and/or proteins. Preferably, the "host organism" is a bacterium, a yeast, or a eukaroytic multicellular living entity (preferably an animal, more preferably a mammal, still more preferably a human).

"Mammals" include, but are not limited to, murines, simians, humans, farm animals, sport animals, and pets.

The terms "polypeptide" and "protein" are used interchangeably and refer to any polymer of amino acids (dipeptide or greater) linked through peptide bonds or modified peptide bonds. Thus, the terms "polypeptide" and "protein" include oligopeptides, protein fragments, fusion proteins and the like. It should be appreciated that the terms "polypeptide" and "protein", as used herein, includes moieties such as lipoproteins and glycoproteins.

An "antibody" (Ab) is protein that binds specifically to a particular substance, known as an "antigen" (Ag) (described infra). An "antibody" is any immunoglobulin, including antibodies and fragments thereof, that binds a specific epitope. The term encompasses polyclonal, monoclonal, and chimeric antibodies (e.g., multispecific antibodies). In nature, antibodies are generally produced by lymphocytes in response to immune challenge, such as by infection or immunization. An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$ and F(v) portions. A small single-chain F(v) comprising the variable (V) region of a light chain may be used, particularly when tissue penetration is desired.

An "antigen" (Ag) is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to, an MHC molecule or T cell receptor. "Antigen processing" refers to the degradation of an antigen into fragments (e.g., the degradation of a protein into peptides) and the association of one or more of these fragments (e.g., via binding) with MHC molecules for presentation by "antigen-presenting cells" to specific T cells.

The term "antigenic material" covers any substance that will elicit an innate or adaptive immune response. As used herein, "a portion of an antigenic material" covers any antigenic material or fragment thereof, which is capable of eliciting an innate or adaptive immune response, even if the fragment is an incomplete representation or subset of the antigenic material as a whole. In one embodiment, it includes the minimal antigen sequence required to elicit a specific immune response (preferably approximately 8-15 amino acid residues in length) when bound to an MHC recognized by a T cell.

An "epitope" or "antigenic determinant" is a structure, usually made up of a short peptide sequence or oligosaccharide, that is specifically recognized or specifically bound by a component of the immune system. It is the site on an antigen recognized by an antibody. For example, as described supra, a T cell epitope is at least a portion of a short peptide derived from a protein antigen during antigen processing by an antigen-presenting cell. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope.

A "chemokine" is a small cytokine involved in the migration and activation of cells, including phagocytes and lymphocytes, and plays a role in inflammatory responses. Examples of chemokines include, but are not limited to, IL8, RANTES, MDC, IP10, MIP1α, and MIPβ.

A "cytokine" is a protein made by a cell that affect the behavior of other cells through a "cytokine receptor" on the surface of the cells the cytokine effects. Cytokines manufactured by lymphocytes are sometimes termed "lymphokines." Examples of cytokines include, but are not limited to, IL1α, IL1β, TNF, IL6, IL12 (p40), and IFNγ.

Chemokines and cytokines can bind to "receptors," which range in specificity from broad recognition (i.e., binding many types of chemokines, cytokines, or other molecules) to highly specific recognition (e.g., binding a small group of related molecules, binding only closely related molecules or only one type of molecule). Examples of "chemokine receptors" include, but are not limited to, CCR2, CCR5, CCR6, and CCR7. Examples of "surface receptors" of interest to the present invention include, but are not limited to, mannose receptor (e.g., C type 1), macrophage scavenger receptor (e.g., scavenger R2), and prolactin receptor.

Expression or secretion of a chemokine, cytokine, receptor, marker, or other protein of interest may be measured, either directly or indirectly, using a wide range of methods known to those of ordinary skill in the art. Methods include protein assays, immunoprecipitation methods, Western blotting and other types of direct or indirect immunoblotting, spectophotometry or ultraviolet (UV) methods. Antibodies specific to cytokines and chemokines, as well as to cell surface antigens and other markers, are commercially available. Depending on the method used, detection may take place using a tagged or labeled protein, a reporter plasmid, a radiolabel (e.g., using a radioactive isotope, such as $^{35}$S-Met or $^{35}$S-Cys), a chemical label or stain, a fluorescent label, an immunolabel, or by other detection methods known in the art. In one preferred embodiment, the detection will be quantitative or capable of quantitation in order to measure levels of the protein. For example, the protein may be detected in blood, in a sample of isolated blood cells (e.g., leukocytes), in lymph, in saliva, or in other types of biological samples. These methods are particularly useful for medical applications of the present invention.

Alternatively, the level of the corresponding mRNA for a given cytokine, chemokine, receptor, marker or other protein of interest may be detected or measured, either directly or indirectly, via a variety of methods known to those of ordinary skill in the art. Similarly, the presence of a DNA having a sequence of interest (e.g., for genetic testing, for DNA fingerprinting, for detection for mutations, and for other purposes known in the art) may be detected or measured. Moreover, the test may also detect or measure the binding of a protein (e.g., a polymerase, an activator, or an inhibitor) to a DNA or mRNA fragment (e.g., a promoter or an enhancer). The test may also detect or measure the binding of a substance (e.g., a drug) to a protein. These methods include, but are not limited to, Northern blotting, hybridization detection (e.g., with oligonucleotides or longer nucleic acid sequences, which may be radiolabeled, chemical labeled, immunolabeled, or fluorescence labeled), or polymerase chain reaction (PCR). PCR methods may be qualitative or, more preferably, quantitative (e.g., quantitative PCR). The mRNA may be detected in vivo, in situ, or in vitro. For example, the protein may be detected in blood, in a sample of isolated blood cells (e.g., leukocytes), in lymph, in saliva, or in other types of biological samples (including cell samples (e.g., bone marrow, lymph nodes). Nucleic acids used for hybridization or for PCR may be specific or degenerate. In addition, they may correspond to the species of animal from which the sample is taken, or the sequence may correspond to a different species (e.g., use of a mouse sequence to probe a rat, human, or chicken sample).

An "isolated" or "purified" population of cells is substantially free of cells and materials with which it is associated in nature. By substantially free or substantially purified APCs is meant at least 50% of the population are APCs, preferably at least 70%, more preferably at least 80%, and even more preferably at least 90% free of non-APCs cells with which they are associated in nature.

An "immunogen" is a substance capable of eliciting an immune response. Each immunoglobulin molecule can potentially bind a variety of antibodies directed at its unique features, or "idiotype," which is comprised of a series of "idiotopes." An "idiotope" is a single antigenic determinant on a variable region of an antibody or T cell receptor. It is the set of idiotopes on an antibody which comprise the idiotype that makes that antibody unique. The "dominant idiotype" is the idiotype found on the major fraction of antibodies generated in response to an antigen.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "prion" is a protein or protein fragment capable of replicating.

A "pathogenic organism" includes a virus, microorganism, or a parasite. A pathogenic organism is capable of triggering an abnormal physiological condition or disease or an abnormal physiological response. A pathogenic organism may be infectious.

"Biological sample" includes samples of tissues, cells, blood, fluid, or other materials obtained from a biological organism. It also includes a biological organism, cell, virus, or other replicative entity. Also included are solid cultures (such as bacterial or tissue cultures). Also included are solid samples, including, but not limited to, food, powder, and other solids, including non-biological solids, containing a biological organism, cell, virus, or other replicative entity. Also included are washing, homogenizations, sonications, and similar treatments of solid samples. Likewise, the term includes non-solid biological samples.

"Non-solid biological samples" include those that are not a tissue or an organ. Examples include, but are not limited to, blood, plasma, serum, mucus, urine, saliva, semen, vaginal discharge, sweat, tears, lymph, gastrointestinal suspensions or fluids, and cerebrospinal fluid. Also included are cultures (such as bacterial or tissue cultures) and phage lysates. Also included are fluid samples, including, but not limited to, water and beverages containing a biological organism, cell, virus, or other replicative entity. Also included are suspensions and colloidal mixtures "Non-biological samples" include samples not obtained from a biological organism, except in instances in which such a sample is contaminated by a biological sample. Non-biological samples may be in liquid, gaseous, or solid form. They may include, but are not limited to, non-biological solid samples, liquid samples, gaseous samples, solutions, suspensions, colloidal mixtures, and aerosols.

"Non-biological solid samples" include samples from a wide variety of items, including, but not limited to, wood, concrete, dirt, plastics, and any other solids that have the potential to become contaminated. These samples may be pulverized, sonicated, minced, chopped, ground, or otherwise broken down into fine particles, and then prepared as a colloidal mixture or suspension prior to separation in the device. More preferably, the non-biological solid sample is dissolved into a solution.

"Non-biological liquid samples" include a wide range of samples, which include, but are not limited to, water, organic solvents, aqueous or organic solutions, and the like.

Methods of dissociating cells, such as cells in tissues, organs, or multi-cellular organisms, include physical, chemical, and enzymatic methods. Examples include, but are not limited to, mincing, homogenizing, sonicating, and grinding, preferably in a physiological buffer, such as described in this specification or known to those of ordinary skill in the art.

One of ordinary skill in the art would easily adapt some of these methods for use in the preparation of non-biological samples.

Preferably, the cells are selected from the group consisting of white blood cells, epithelial cells, buccal cells, tissue culture cells, semen, vaginal cells, urinary tract cells, colorectal cells, plant cells, bacterial cells, and yeast cells.

In one embodiment, the present method may be applied advantageously to any whole cell suspension. Alternatively, the cells may be lysed to release organelles and/or nucleic acid prior to exposure to the test strip.

The detection process may comprise use of an indicator. The signal generated by the indicator of the present invention provides positive identification of the presence of a given nucleic acid or protein on the substrate. For example, nucleic acids can be detected (and preferably quantified) by the use of a specific or non-specific nucleic acids probe or other signal generators and one of the versions of immunoassay. Proteins can be detected (and preferably quantified) by the use of an immunoassay. Preferably, the indicator comprises a fluorescent indicator, a color indicator, or a photometric indicator. Alternatively, antibodies conjugated with biotin and polyavidin-horse radish peroxidase (HRP) may be used, or an assay using polyethyleneimine-peroxidase conjugate (PEI-PO), which interacts with DNA, may be used, as known in the art. Other methods of detection will occur to those of ordinary skill in the art.

In some embodiments, particularly in photosensitive embodiments, it may be necessary to provide an upper housing and a lower housing that inhibit exposure to light in general and/or to certain wavelengths of light in particular. If the indicator is not already present on the test strip, it may be added and, if necessary, incubated with the test strip material in the housing. The indicator is easily drawn through the test strip material and discarded. Blocking agents and washes may likewise be circulated through the test strip material, although in preferred embodiments, blocking is not necessary. When the preparation steps are complete, the housing is opened in the absence of light (or in the absence light of the wavelength for the indicator reaction), and the test strip material is the exposed to the light of the desired wavelength to trigger the photometric reaction.

A "physiological condition" may be normal or abnormal. The physiological condition may result from the genetic make-up of the organism (including, but not limited to, the expression of various proteins), from environmental factors (including, but not limited to, the ingestion of drugs, poisons, food, and beverages and the exposure of an organism to toxic or non-toxic substances), from disease (both infectious or non-infectious), from an injury, from a metabolic disorder, from pregnancy or nursing, and from a wide range of other circumstances known in the art. Examples include, but are not limited to, pregnancy, nursing, acquired immune deficiency syndrome (AIDS; such as by infection with human immunodeficiency virus (HIV)) or other sexually transmitted diseases (e.g., syphilis, gonorrhea, herpes), tuberculosis, Ebola, malaria, Lassa fever, hepatitis (A, B, C, D, or E), dengue fever, pneumonia (e.g., bacterial, viral), and genetic diseases, syndromes, or polymorphisms with respect to the genotype and/or phenotype of the organism.

For example, it is well-known in the art that a pregnant human female has elevated levels of human chorionic gonadotropin (hCG) in her blood and urine and that hCG can be used as a marker for pregnancy testing.

Examples of an "abnormal physiological condition or disease" and an "abnormal physiological response" include, but are by no means limited to, cancer or growth of a non-immunogenic tumor, allergy, asthma, an autoimmune disease, an infectious disease, and inflammation. Cancer and non-immunogenic tumor cells are often characterized by abnormal protein expression, including expression of proteins encoded by mutated nucleotide sequences, abnormal levels of protein expression, or inappropriate expression of proteins. Allergies and asthma (especially allergy-related asthma) are often characterized by aberrant accumulation of mast cells, bone marrow-derived cells which degranulate to release histamines and which synthesize histamines in response to aberrant activation by a number of stimuli (e.g., IgE) in response to allergens. Autoimmune diseases are directed against "self" antigens and are characterized by abnormal levels of MHC class II cells and autoreactive T cells (especially $CD4^+$ and $CD8^+$ T cells). Infection by an infectious disease triggers an immune response. Inflammation, which may be due to an infection, an injury, or an autoimmune disorder, triggers a response similar to the immune response. These conditions are characterized by up-regulation of some proteins and down-regulation of others.

The terms "cancer" and "neoplasm" are used interchangeably and in either the singular or plural form, refer to cells that have undergone a malignant transformation that makes them pathological to the host organism. The definition of a cancer cell, as used herein, includes not only a primary cancer cell, but any cell derived from a cancer cell ancestor. This includes metastasized cancer cells, and in vitro cultures and cell lines derived from cancer cells. The term "tumor," in either singular or plural form, includes both "cancer" and "neoplasm" and also includes non-malignant, but aberrant, growths of cells. The distinction between cancer/neoplasm tumor cells and non-malignant tumor cells may be determined using various tests, especially histological examination.

An "effective amount" is an amount sufficient to affect beneficial or desired results. An effective amount may be administered one or more times to achieve the beneficial or desired result.

As used herein, a "therapeutically effective amount" is used herein to mean an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as the size of a tumor mass, antibody production, cytokine, fever or white cell count. Additionally, the therapeutically effective amount is an amount sufficient to increase by at least about 30 percent, more preferably by at least 50 percent, most preferably by at least 90 percent, a clinically significant feature of pathology, such as cytokine production.

As used herein, a "drug" may be a medicament or other treatment for a physiological condition or it may be any substance taken to alter a physiological condition. "Drugs" include, but are not limited to, chemical, biological, radiological, and other medicaments, treatments, pharmaceuticals, or substances (other than food) taken to alter a physiological condition. A "drug" also includes a therapeutic agent or a substance, other than food, which is used in the prevention, diagnosis, alleviation, treatment, or cure of disease.

As used herein, "metabolism" includes "biotransformation," and "drug metabolism" refers to "biotransformation of drugs." "Metabolism" also refers to the sum of the chemical and physical changes occurring in tissue, consisting of anabolism (reactions that convert small molecules into large molecules) and catabolism (reactions that convert large molecules into small molecules), including both endogenous large molecules as well as biodegradation of xenobiotics. Similarly, "drug metabolism" includes biodegradation of drugs. "Primary metabolism" refers to metabolic processes central to most cells (e.g., biosynthesis of macromolecules, energy production, turnover, etc.). "Secondary metabolism" refers to metabolic processes in which substances (such as pigments, alkaloids, terpenes, etc.) are only synthesized in certain types of tissues or cells or are only synthesized under certain conditions.

As used herein, a "metabolite" or "metabolin" includes "any substance produced by metabolism or by a metabolic process," and "drug metabolite" or "drug metabolin" includes any substance produced by drug metabolism or by a metabolic process resulting from administration of a drug. A "metabolite" or "metabolin" also includes any product (foodstuff, intermediate, waste product) of metabolism, particularly of catabolism, either "primary" or "secondary." A "primary metabolite" is synthesized in a step in primary metabolism, while a "secondary metabolite" is synthesized in a step in secondary metabolism. A "drug metabolite" or "drug metabolin" also includes any product of drug metabolism.

It is envisioned that the present invention is useful for the testing of the interaction of drugs with various proteins and other ligands.

It is also envisioned that the present invention is useful for the testing of a biological sample for the presence of drugs, based on their known interactions with various ligands.

The term "integrity maintainer" or "integrity maintenance means" as used herein means a sealable member that prevents degradation and/or loss of the matrix. Preferably, the integrity maintainer of the present invention creates an air tight seal, thus preventing air, bacteria or other contaminants from coming into contact with the matrix and purified nucleic acid. The integrity maintainer can be in the form of a plastic bag, with or without a seal, cellophane, a sealable container, parafilm and the like.

When not otherwise stated, "substantially" means "being largely, but not wholly, that which is specified."

Various aspects and embodiments of the present invention will now be described in more detail by way of example. Other examples will suggest themselves to one of ordinary skill in the pertinent art. These examples are intended merely to be illustrative of the present invention and are not intended to limit the invention in any way. It will be appreciated that modification of detail may be made without departing from the scope of the invention.

EXAMPLES

Example 1

Comparison of FUSION 5™ Absorbency with Other Materials

The absorbency of FUSION 5™ (Whatman plc), which can be used as the hydrophilic matrix in a preferred embodiment of the present invention, was compared with those of three other materials (CF3, CF4, and CF5), which are commonly used as industry standards. CF3, CF4, and CF5 are cellulose absorbents typically used in industry for lateral flow assays and are well-known in the art.

Protocol:

10 ml of deionized water was placed into a Petri dish. A 5 cm² piece of the absorbent was weighed before being placed into the water and left for 10 seconds. The absorbent was removed and the reweighed. Subtracting the dry weight from the wet weight gives the water absorbency for a 5 cm² piece. This was performed 5 times for each absorbent.

Figure 3:
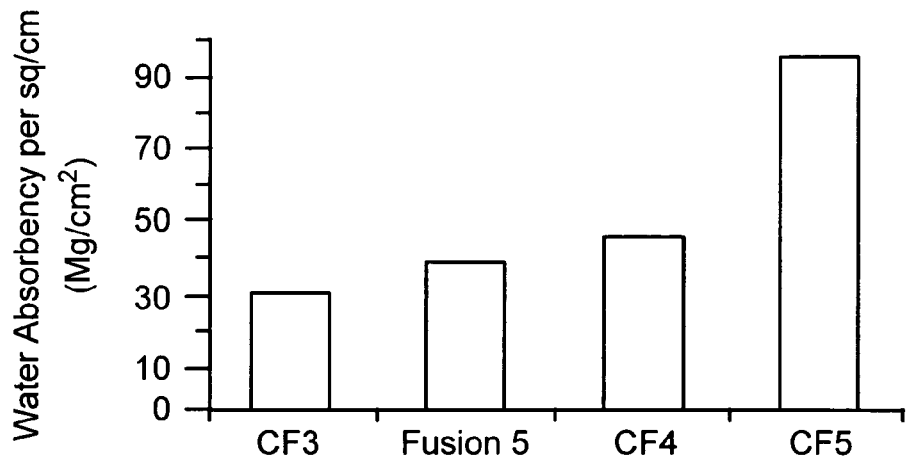
FIG. 3 is a bar graph depicting the results of an experiment to measure the water absorbency ($mg/cm^2$) of one embodiment of the test strip hydrophilic matrix compared to other materials.

Results:

The results of the experiment are shown in the bar graph of FIG. 3. The range of water absorbency per square centimeter for the three other materials was from approximately 30 mg/cm² to nearly 100 mg/cm², while the absorbency of the FUSION 5™ material was 40 mg/cm² (see Table 2).

TABLE 2

| Material | Water Absorbency (mg/cm²) |
| --- | --- |
| FUSION 5 ™ | 40 mg/cm² |
| CF3 | 31 |
| CF4 | 46 |
| CF5 | 98 |

These results demonstrate that the water absorbency of the FUSION 5™ material is within the range for water absorbencies of materials used as industry standards.

Example 2

Comparison of FUSION 5™ Wicking Rate with Nitrocellulose Membranes

The wicking rate of FUSION 5™ (Whatman plc), which can be used as the hydrophilic matrix in a preferred embodiment of the present invention, was compared with the wicking rates of three nitrocellulose membranes (RP, FP, and SP). Among the nitrocellulose membranes, the RP membrane had the largest average pore size, while the SP membrane had the smallest average pore size.

Protocol:

10 ml of deionized water was placed in a Petri dish. The wicking materials were cut to 5 cm lengths, with a make drawn using a soft pencil at 0.5 mm from the top and bottom edge. The wicking material was suspended from a clamp stand vertically, and lowered into the water until the water reached the 0.5 mm mark. The time for the water to wick to the top mark was recorded. This was repeated 3 times for each material.

Figure 4:
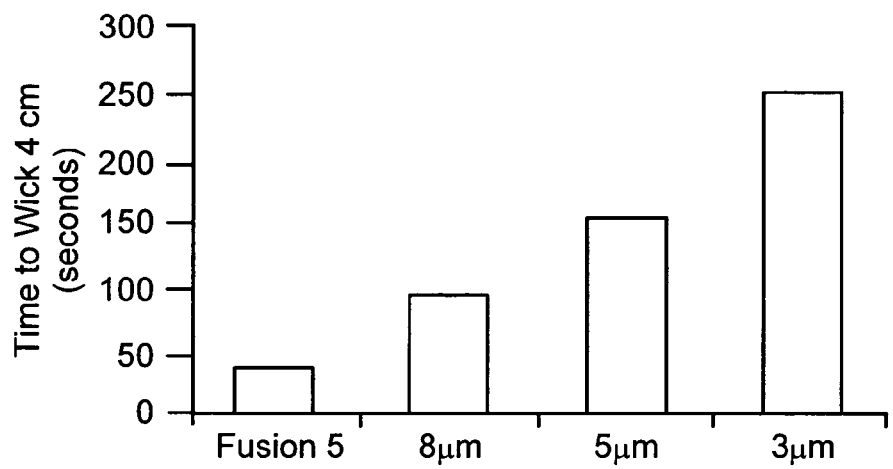
FIG. 4 is a bar graph depicting the results of an experiment to measure the wicking rate (seconds) of 4 cm of one embodiment of the test strip hydrophilic matrix compared to three types of nitrocellulose membranes.

Results:

The results of the experiment are shown in the bar graph of FIG. 4. The wicking rate for each sample was measured as the time (seconds) needed to wick 4 centimeters of material. Four centimeters of the FUSION 5™ sample was wicked in 40 seconds, compared with the RP, FP, and SP nitrocellulose membranes (see Table 3). These results demonstrate the superior sample wicking rate of the FUSION 5™ material (a polymer/glass fiber matrix) over those of the nitrocellulose membranes tested.

TABLE 3

| Material | Wicking Rate for 4 cm (seconds) |
| --- | --- |
| FUSION 5 ™ | 40 seconds |
| RP | 87 |
| FP | 175 |
| SP | 238 |

Additional testing of FUSION 5™ yielded a wicking rate of 140 seconds for 7.5 cm.

Example 3

Conjugate Release of FUSION5™ Using Gold and Latex Carrier Beads

The conjugate release properties of FUSION 5™ were explored as a comparison between the release of gold carrier beads and latex carrier beads.

Protocol:

The conjugate (40 nm gold conjugate from Alchemy Labs, Dundee, UK; 288 nm dyed latex, Estapor, Paris, France) was diluted in either 18.2 MΩ water (MilliQ) or the appropriate buffer to a known optical density (OD10 at 520 nm). The conjugate (60 µl) was applied to a segment of FUSION 5™ conjugate pad from a pipette and the conjugate pad was dried to a consistent level of dryness (2 hours at 37° C. followed by storage for a minimum of 12 hours over dried silica gel). The amount of release was measured by placing the conjugate pad in 18.2 MΩ water (1 ml in a test tube), the amount of conjugate release was measured by reading the absorption in a spectrophotometer at 520 nm for gold and 280 nm for latex.

Figure 5:
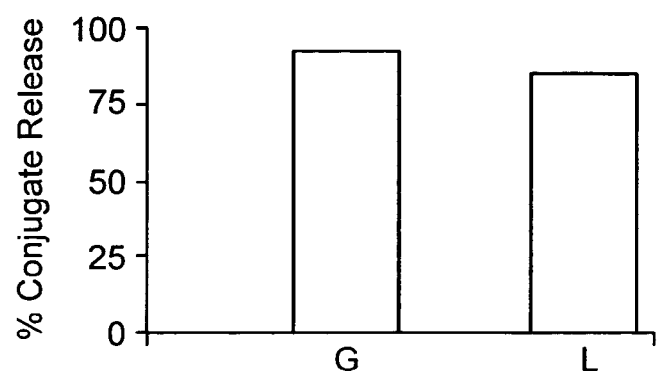
FIG. 5 is a bar graph depicting a comparison of conjugate release (%) of the labeled binding reagent from the hydrophilic matrix, where the labeled binding reagent comprises a gold carrier bead (G) or a latex carrier bead (L).

Results:

The results of the experiment are shown in the bar graph of FIG. 5. After 45 seconds of exposure to water in the test tube, spectrophotometric measurements showed >94% release of the gold conjugate carrier beads (G) and >83% release of the latex conjugate carrier beads (L).

Example 4

Use of FUSION 5™ as a Blood Separator

A FUSION 5™ blood separator was prepared and used as a blood separator.

Protocol:

The blood separator was cut into strips 0.5×5 cm and each strip was weighed. Whole blood was applied to the surface (40 µl) was loaded onto the separator and the blood was allowed to separate laterally. Once separation was complete the plasma containing section was cut off and weighed. The time for the separation to be complete was recorded. The plasma containing material was transferred to a centrifugal separator with a polypropylene mesh (Whatman 6838-0005). The plasma was spun out of the filter at 13000 rpm for 20 minutes, and analysed for all analytes using commercially available tests (Sigma, St Louis). Each test was repeated 10 times. The results reported are for blood obtained from a 36% hemoatocrit female.

Results:

In a lateral flow format, the FUSION 5™ strip had an 86% efficiency (serum recovery), and in a vertical flow format, the FUSION 5™ strip had a 67% efficiency (serum recovery). There was no evidence of analyte removal.

The results of the use of the lateral flow format as a blood separator are shown in Table 4, as a comparison with centrifuged serum.

TABLE 4

| % Available to Test* | FUSION 5 ™ |
| --- | --- |
| Volume Serum | 86% |
| Total Protein* | 98% ± 1.7% |
| IgG* | 99% ± 1.1% |
| Cholesterol* | 101% ± 2.1% |

*Versus centrifuged serum

Example 5

Additional Properties of FUSION 5™ Material

Additional properties of FUSION 5™ were studied. Results are shown in Table 5.

TABLE 5

| TEST/PROPERTY | RESULT(S) |
| --- | --- |
| Thickness (µm @ 5 KPa) | 370 |
| Klemm Wicking (7.5 cm) | 2:40 (min/sec) |
| Maximum Pore Size (µm) | 11.0 |
| Average Pore Size (µm) | 4.6-5.6 |
| Water Absorption (mg/cm$^2$) | 40 |
| Particle Retention (µm) | 2.3 |
| % Release of Gold Conjugate | >94 |
| % Release of Latex Conjugate | >83 |
| % Available Serum Obtained | 86 |

Example 6

Use of FUSION 5™ with Whole Blood for a Pregnancy Test

A. Preparation of FUSION5™ for a Pregnancy Test:

Take a reel of FUSION 5™ that is 8 cm wide and 50 m long. Laminate the FUSION 5™ matrix to a PE card coated with a pressure sensitive to provide additional mechanical strength during handling.

Test Line:

At the capture zone (approximately 2.5 cm from the edge of the material) apply 2 micron latex beads conjugated to a monoclonal anti-alpha hCG antibody to the FUSION 5™ matrix from a suitable buffer (e.g., 10 mM phosphate pH 7.2).

Control Line:

At the control zone (approximately 2.7 cm from the edge of the material) apply 2 micron latex beads conjugated to a goat anti-Mouse IgG antibody to the FUSION 5™ matrix from a suitable buffer (e.g., 10 mM phosphate pH 7.2).

Conjugate Release:

At the conjugate release zone (approximately 1 cm from the edge of the material) apply a 150 nm blue dyed latex colloid conjugated to a monoclonal anti-beta hCG antibody to the FUSION 5™ matrix from a suitable buffer (see above).

After application of the lines (that may be done simultaneously) dry the striped FUSION 5™ material for at least 3 hours at 37° C.

Cut the FUSION 5™ into 5 mm wide strips, and place in a plastic housing.

B. Use of the FUSION5™ Pregnancy Test Strip with Whole Blood

Apply 100 microlitres of whole blood to the test strip. As the whole blood sample wicks up the strip, the cellular component of the blood will be captured by the FUSION 5™, allowing the acellular component to flow without the red cells. The acellular component will reach the conjugate release zone and resuspend the blue latex conjugate, and any hCG present will interact with the anti-beta hCG present on the conjugate. The sample and resuspended conjugate will continue to flow to the capture line, where any hCG present will attach to the anti-alpha hCG antibody present on the capture line, forming a sandwich resulting in the dyed latex being retained at the capture line. A positive result (indicated by the appearance of a blue line at the capture line) will indicate the presence of elevated levels of hCG (a hormone associated with pregnancy in humans). At the control line the anti-mouse IgG will interact with the monoclonal antibody on the conjugate. The control line will turn blue whether there are elevated levels of hCG present or not.

Example 7

Protocol for Use of FUSION 5™ with Urine for a Pregnancy Test

A. Preparation of FUSION5™ for a Pregnancy Test:

Take a reel of FUSION 5™ that is 8 cm wide and 50 m long. Laminate the FUSION5™ matrix to a PE card coated with a pressure sensitive to provide additional mechanical strength during handling.

Test Line:

At the capture zone (approximately 2.5 cm from the edge of the material) apply 2 micron latex beads conjugated to a monoclonal anti-alpha hCG antibody to the FUSION5™ matrix from a suitable buffer (e.g., 10 mM phosphate pH 7.2).

Control Line:

At the control zone (approximately 2.7 cm from the edge of the material) apply 2 micron latex beads conjugated to a goat anti-mouse IgG antibody to the FUSION5™ matrix from a suitable buffer (e.g., 10 mM phosphate pH 7.2).

Conjugate Release:

At the conjugate release zone (approximately 1 cm from the edge of the material) apply a 40 nm gold colloid conjugated to a monoclonal anti-beta hCG antibody to the FUSION 5™ matrix from a suitable buffer (see above).

After application of the lines (that may be done simultaneously) dry the striped FUSION 5™ material for at least 3 hours at 37° C.

Cut the FUSION5™ into 5 mm wide strips, and place in a plastic housing.

B. Use of the FUSION5™ Pregnancy Test Strip with Urine

Apply 100 microliters of urine to the test strip. The urine will flow up the strip until it reaches the capture zone. The urine will resuspend the conjugate, and allow interaction of the urine sample with the conjugate. Any hCG present will bind to the gold conjugate present. The samples and resuspended gold conjugate will flow towards the capture line, where a positive result (indicated by the appearance of a red line at the capture line) will indicate the presence of elevated levels of hCG (a hormone associated with pregnancy in humans). The control line will turn red whether there are elevated levels of hCG present or not.

Any excess gold will flow past the lines and be retained at the top of the test strip.

Example 8

Dispensing Test and Control Lines, Spraying and Drying of Protein A Gold Conjugate for Human IgG Assay on FUSION 5™ Membrane FUSION5™ test strips were made using the following protocol.

A. Items Needed:

| Name | Suggested Manufacturer |
|---|---|
| FUSION 5 ™ membrane | Whatman |
| 60 mm backing | G&L (Los Angeles, CA) |
| Latex-Protein A @ 20 mg/ml | DCN (San Diego, CA) |
| Latex-Mouse IgG @ 20 mg/ml | DCN |
| Cellulose grade 470 | Schleicher & Schuell |
| Protein A Gold Conjugate, OD = 20.0 | DCN |
| Goat anti-mouse Gold Conjugate, OD = 10.0 | DCN |
| Appropriate buffer and stabilizing agents, as described below | Sigma or other provider |

(Optical density (O.D.) was measured at 520 nm)

B. Equipment Needed:

BIODOT™ AD5000™ with 100 μm ceramic tip, vacuum pump and wash station Script to control the application of the liquids onto FUSION 5™ membrane Probe sonicator Mini-Vortexer 96-well source plate XYZ3050 (an XY bed that moves the membrane relative to the print heads to create a line) with AIR-JETQUANTI3000™ dispenser Drying oven BIODOT™ CM4000™ Cutter Slitter or paper cutter 5 mm Cassettes Rocker Desiccant Foil pouch(es)

C. Test Card/Strip Preparation

1. Record the details of the batch above.
2. Cut FUSION 5™ membrane to 44 mm strip(s).
3. Laminate a 44 mm strip of FUSION 5™ membrane onto the backing card so that it is aligned with the bottom edge of the card.
4. Turn on AD5000 and computer. Load script to control the application of the liquids onto the FUSION 5™ membrane.
5. Sonicate the test and control line reagents for 1 minute each. Vortex. Pipette each reagent into the appropriate source well of the 96-well plate. Each card will use about 200 μl of each reagent.
6. Run the script.
7. Add 20% w/v Sucrose and 5% w/v Trehalose to both the Protein A gold conjugate at OD=20.0 and the Goat anti-mouse gold conjugate at OD=10.0. (Here, DCN storage buffer was used. A 10 mM borate solution, pH 8.2, could also be used. Often a conjugate manufacturer will provide, designate, or define a buffer.) Place on rocker until completely dissolved or suspended.
8. Spray the Protein A gold conjugate at OD=20.0 at a rate of 10 μl/cm, psi~1, micrometer opening=1.0. Perform 1 overspray again at 10 μl/cm.
9. Dry card(s) for 1 hour at 37° C.
10. Spray the Goat anti-mouse gold conjugate at OD=10.0 at a rate of 10 μl/cm, psi~1, micrometer opening=1.0. Perform 1 overspray again at 10 μl/cm.
11. Dry card(s) for 1 hour at 37° C.
12. Cut the cellulose grade 470 into 18 mm strip(s) and laminate it so that it is aligned with the top of the card.
13. Because of line ramping issues, mark off the first 15 mm of each line. Orient the card so that the wick is on top. Align a ruler on the wick so that '0' is on the left side of the card. Mark off 15 mm lines starting at these points: 58 mm, 115 mm, 173 mm, and 231 mm. Discard these sections after cutting the card into strips with cutter.
14. Cut card into 5 mm strips.
15. Store in a heat-sealed, desiccated foil pouch until ready to test.

Example 9

Testing Human IgG Assay with FUSION 5™ Test Strips

A. Items Needed:

Name

Human IgG Assay, FUSION 5™ Test Strips
Normal Human Plasma
1X PBS/0.1% TWEEN™ 20*

*1X Phosphate Buffered Saline (PBS)/0.1% TWEEN™ 20 is prepared from 10X PBS (137 mM NaCl; 2.7 mM KCl; 5.4 mM Na$_2$HPO$_4$; 1.8 mM KH$_2$PO$_4$; pH 7.4) and TWEEN™ 20. TWEEN™ 20 (Sigma) is known by the names of sorbitan mono-9octadecenoate poly(oxy-1,1-ethanediyl),polyoxyethylenesorbitan monolaurate, and polyoxyethylene (20) sorbitan monolaurate.

B. Equipment Needed:

Pipettes

Test tubes

C. Testing

1. For every positive strip to be run, pre-mix 1 μl of normal human plasma or serum with 149 μl of running buffer and add to the sample entry port of each cassette.
2. For every negative strip to be run, add 150 μl of running buffer.
3. Run each strip for 15 minutes; record results after the strip has run for 15 minutes.

Example 10

Human Immunoglobulin Assay on FUSION 5™ Membrane

Material Specifications:

| Sample/Conjugate pad: FUSION 5 ™, width = 44 mm (Whatman) |  |
|---|---|
| Membrane |  |
| Test line reagent: | Latex-Protein A @ 20 mg/ml & 2.016 μl/cm, DCN |
| Control line reagent: | Latex-Mouse IgG @ 20 mg/ml & 2.016 μl/cm, DCN |
| Gold conjugates: | Protein A Gold Conjugate, OD = 20.0, DCN |
| | Goat anti-mouse Gold Conjugate, OD = 10.0, DCN |
| | (Optical density (OD) was measured at 520 nm.) |
| Top pad: | Cellulose 470, width = 18 mm, Schleicher & Schuell/Whatman |
| Backing card | 60 mm backing, G &L |
| Cassettes: | 5 mm Cassettes, DCN |

| Name | Vendor Suggested (if any) | Part Number |
|---|---|---|
| Protein A Gold Conjugate, OD = 20.0 | DCN | PACO-010 |
| Goat anti-mouse Gold Conjugate, OD = 10.0 | DCN | PACG-010 |
| Appropriate buffer and stabilizing agents, as described below | Sigma | |
| 1xPBS | Sigma | P-3813 |
| TWEEN™ 20 | Sigma | P-1379 |

(Optical density (O.D.) was measured at 520 nm.)

Example 11

Human IgG Assay on a Membrane-Standard Operating Procedures

A. FUSION 5™ Membrane-Material Specifications

| Sample/Conjugate pad/: FUSION 5 ™, width = 44 mm, Whatman |  |
|---|---|
| Membrane |  |
| Test Line antibody: | Latex-Protein A @ 20 mg/ml & 2.016 μl/cm, DCN |
| Control line antibody: | Latex-Mouse IgG @ 20 mg/ml & 2.016 μl/cm, DCN |
| Top pad: | Cellulose 470, width = 18 mm, S&S |
| Backing card | 60 mm backing, G&L |
| Cassettes: | 5 mm Cassettes, DCN |
| Running Buffer: | 1xPBS, pH = 7.4, 0.1% Tween 20 |

B. Latex-Protein A Conjugate and Latex-Mouse IgG Conjugate

The capture antibodies are conjugated to latex. The antibodies will serve to capture the analyte (Human IgG) and the gold conjugates, while the latex serves to anchor the antibodies to their position on the test and control lines. The latex is white and is barely visible against the white background of the FUSION 5™ membrane.

These conjugates will be denatured when run through the micro-solenoid valve of the BIOJET™ valve. For this reason, the reagent should be aspirated for dispensing, and there is a limited amount of volume that can be aspirated before the reagent reaches the micro-solenoid valve. Therefore, the test and control lines are striped by juxtaposing shorter ~58 mm lines. Typically, aspiration and dispense operations entail the use of a 'pre-dispense' that primes the dispenser to dispense the actual rate indicated before dispensing onto the actual card. This procedure limits the amount of 'line-ramping' on the test card. Because there is a limited amount of reagent, this step must be by-passed, and an extra step after striping must be added in order to discard the area where 'line-ramping' usually occurs. A specially equipped BIODOT™ AD5000 should enable the user to aspirate more volume before the reagent enters the micro-solenoid valve, which would thus limit the amount of 'line-ramping' on the test card.

C. 5 mm Cassettes

Use of a 5 mm cassette permits a strip configuration that lacks a sample pad. On standard lateral flow test strips, one important function of the sample pad is to slowly introduce analyte and buffer to the rest of the strip. "Flooding" of the strip can occur in its absence, causing analyte and buffer to flow over the membrane rather than through it. The cassette serves to meter the flow of testing fluid allowing it to slowly run up the strip. It does this by compacting the strip after the sample entry area and thus gradually introducing the testing fluids to the rest of the strip.

D. Drying

Drying helps lengthen shelf life. Incomplete drying will result in test deterioration. Every component should be fully dry, especially the desiccants. Every desiccant is re-dried and the use and exposure of the desiccants is controlled. Packing should be done at a low humidity, ideally <20% relative humidity (R.H.). Test and desiccant exposure should be minimal, preferably a few minutes as a maximum.

E. Assay Procedure

For a positive test result kit, pre-mix 1 µl of normal human plasma with 149 µl of running buffer. Add the entire amount to the sample entry port. For a negative test result kit, add 150 µl of running buffer to the sample entry port. Allow the strip to develop for 15 minutes. Where a wicking pad is used, top the assay by peeling off the wicking pad at the top of the strip (removing strip from the inside of the cassette). Read the results at approximately 15 minutes.

Examples 12-14

Different Capture Antibodies or Nucleotides on the Same Platform

The test strip can have multiple capture lines, each with a different capture antibody. In Example 12, each capture line is directed to a different test for the same disease. In Example 13, each capture line is directed to a different test, with each test directed to a different variant or strain of a disease or to a different disease in a family of closely related diseases. In Example 14, each capture line is directed to a test for a different disease.

Example 15

Simultaneous Testing of HIV, Tuberculosis, and/or Malarial Infection

The test strip has multiple capture lines for patient testing for infectious disease using a single blood sample. One line tests for infection of the patient with human immune deficiency virus (HIV), which causes acquired immune deficiency syndrome (AIDS); another tests for infection with tuberculosis; and another tests for malaria.

Variations, modifications, and other implementations of what is described herein will occur to those of ordinary skill in the art without departing from the spirit and scope of the invention.

The foregoing examples demonstrate experiments performed or contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove and hereinbelow, are hereby expressly incorporated herein by reference to the extent that they describe, set forth, provide a basis for or enable compositions and/or methods which may be important to the practice of one or more embodiments of the present inventions.

REFERENCES

1. U.S. Pat. No. 5,622,871 (granted 22 Apr. 1997)
2. U.S. Pat. No. 4,477,575 (granted 16 Oct. 1984)
3. U.S. Pat. No. 4,703,017 (granted 27 Oct. 1987)
4. U.S. Pat. No. 5,075,078 (granted 24 Dec. 1991)
5. U.S. Pat. No. 4,313,734 (granted 2 Feb. 1982)

What is claimed is:

1. A test strip for detecting the possible presence of an analyte in a liquid sample applied to the test strip, the test strip comprising a dry porous medium comprising a single monolithic hydrophilic matrix, wherein the single monolithic hydrophilic matrix comprises:
   a. a network of fibers comprising a mixture of polymer and glass fiber or glass microfiber; and
   b. a series of zones comprising:
      i. a sample application zone;
      ii. a conjugate release zone comprising a labeled binding reagent, wherein
         at least a portion of the labeled binding reagent specifically binds to the analyte;
         the labeled binding reagent comprises a label;
         the labeled binding reagent specifically binds to the analyte to form a first complex comprising the labeled binding reagent and the analyte; and
         the labeled binding reagent is dry on the test strip prior to application of the liquid sample and is released into mobile form upon contact with the liquid sample;
      iii. a capture test zone comprising a capture test reagent, wherein
         at least a portion of the capture test reagent specifically binds either to the analyte or to the first complex;
         the capture test reagent specifically binds either to the analyte or to the first complex to form a second complex comprising the labeled binding reagent, the analyte, and the capture test reagent; and
         the capture test reagent is dry on the test strip prior to application of the liquid sample and is largely immobile;
      iv. a capture control zone comprising a capture control reagent, wherein
         at least a portion of the capture control reagent binds to the labeled binding reagent;
         the capture control reagent binds to the labeled binding reagent to form a third complex comprising the labeled binding reagent and the capture control reagent; and
         the capture control reagent is dry on the test strip prior to application of the liquid sample and is largely immobile; and
      v. an absorbent zone, wherein the absorbent zone draws the liquid sample through the dry porous medium of the test strip by capillary action.

2. The test strip of claim 1, wherein the single hydrophilic matrix comprises a mixture of glass fiber and polymer.

3. The test strip of claim 2, wherein the polymer comprises polyester, polyethylene, polypropylene, latex, polyether sulfone, polyvinylidene fluoride, polyethylene, nylon, or polytetrafluoroethylene, or cellulose acetate.

4. The test strip of claim 2, wherein the polymer comprises latex.

5. The test strip of claim 1, wherein the single hydrophilic matrix further comprises a binder.

6. The test strip of claim 5, wherein the binder is selected from the group consisting of polyvinylacrylamide, polyvinylacrylate, polyvinylalcohol, polystyrene, polymethylmethacrylate, and gelatin.

7. The test strip of claim 1, wherein the single hydrophilic matrix has a wicking rate of at least 4 cm in 100 seconds for water.

8. The test strip of claim 7, wherein the wicking rate is in the range of at least 4 cm in 60 seconds for water.

9. The test strip of claim 8, wherein the wicking rate is in the range of at least 4 cm in 50 seconds for water.

10. The test strip of claim 1, wherein the single hydrophilic matrix has an average pore size in the range of 1.5 microns to 25.0 microns.

11. The test strip of claim 10, wherein the single hydrophilic matrix has an average pore size in the range of 2.0 microns to 7.0 microns.

12. The test strip of claim 10, wherein the average pore size is in the range of 3.0 microns to 6.0 microns.

13. The test strip of claim 1, wherein the single hydrophilic matrix has a thickness of between 50 microns and 1000 microns.

14. The test strip of claim 13, wherein the single hydrophilic matrix has a thickness of between 150 microns and 500 microns.

15. The test strip of claim 1, wherein the portion of the labeled binding reagent that specifically binds to the analyte comprises a ligand that specifically binds to the analyte.

16. The test strip of claim 15, wherein the labeled binding reagent further comprises a solid support to which the ligand is attached.

17. The test strip of claim 16, wherein the solid support comprises gold, latex, selenium, platinum, copper, or iron.

18. The test strip of claim 16, wherein the solid support comprises a carrier bead.

19. The test strip of claim 18, wherein the size of the carrier bead allows the carrier bead to move through the matrix and wherein the bead is mobile within the matrix when the bead and the matrix are wet.

20. The test strip of claim 18, wherein the diameter of the carrier bead is 10% or less than the average pore size of the matrix.

21. The test strip of claim 18, wherein
a. the average pore size of the matrix is in the range of 4 to 6 micrometers; and
b. the carrier bead comprises a gold bead having a diameter in the range of 20-80 nanometers.

22. The test strip of claim 18, wherein
a. the average pore size of the matrix is in the range of 4 to 6 micrometers; and
b. the carrier bead comprises a latex bead having a diameter in the range of 100-800 nanometers.

23. The test strip of claim 18, wherein the carrier bead comprises a latex bead comprising a colorimetric dye, a fluorescent dye, a paramagnetic core, a plasmon resonant particle, or a quantum dot.

24. The test strip of claim 1, wherein the label of the labeled binding reagent comprises a colorimetric indicator, a fluorescent indicator, a photometric indicator, a radioactive indicator, an immunological indicator, or a dye.

25. The test strip of claim 15, wherein the ligand is selected from the group consisting of:
a. a polypeptide, an oligopeptide, an antigen, an antibody, or a prion;
b. a nucleic acid or a peptide nucleic acid;
c. a drug, an analog of a drug, or a drug metabolite; and
d. an imprinted polymer.

26. The test strip of claim 15 wherein the ligand is selected from the group consisting of:
a. a nucleic acid having a sequence of at least 65% complementarity to a target sequence of interest;
b. an antibody that specifically binds to an antigen;
c. an antigen that specifically binds to an antibody;
d. an oligopeptide that specifically binds to a protein;
e. a protein that binds to a drug or an analog of a drug;
f. a drug or an analog of a drug; and
g. an imprinted polymer that specifically binds to:
  i. a polypeptide, an oligopeptide, an antigen, an antibody, or a prion;
  i. a nucleic acid or peptide nucleic acid; or
  ii. a drug, an analog of a drug, or a drug metabolite.

27. The test strip of claim 1, wherein the portion of the capture test reagent that specifically bind either to the analyte or to the first complex comprises a ligand that specifically binds to the analyte or to the first complex.

28. The test strip of claim 27, wherein the binding of the ligand to the analyte or to the first complex concentrates the analyte or the first complex.

29. The test strip of claim 27, wherein the ligand is selected from the group consisting of:
a. a polypeptide, an oligopeptide, an antigen, or an antibody;
a. a nucleic acid or a peptide nucleic acid;
b. a drug, an analog of a drug, or a drug metabolite; and
c. an imprinted polymer.

30. The test strip of claim 27, wherein the ligand is selected from the group consisting of:
a. a nucleic acid having a sequence of at least 65% complementarity to a target sequence of interest;
b. an antibody that specifically binds to an antigen, wherein the antibody does not significantly bind to the labeled binding reagent in the absence of the analyte;
c. an antigen that specifically binds to an antibody, wherein the labeled binding reagent does not significantly bind to the antigen in the absence of the analyte;
d. an oligopeptide that specifically binds to a protein, wherein the labeled binding reagent does not significantly bind to the oligopeptide in the absence of the analyte; and
e. an imprinted polymer, wherein the labeled binding reagent does not significantly bind to the imprinted polymer in the absence of the analyte.

31. The test strip of claim 1, wherein the portion of the capture control reagent that binds to the labeled binding reagent comprises a ligand that specifically binds to the labeled binding reagent.

32. The test strip of claim 31, wherein the binding of the ligand to the labeled binding reagent concentrates the labeled binding reagent to enable detection of the label indicating the presence of the third complex.

33. The test strip of claim 32, wherein:
a. the labeled binding reagent has an overall negative charge; and
b. the capture control reagent has an overall positive charge.

34. The test strip of claim 32, wherein:
a. the labeled binding reagent further comprises a negatively charged gold carrier bead; and
b. the capture control reagent comprises:
  i. a positively charged polymer; or
  ii. a positively charged ligand.

35. The test strip of claim 32, wherein:
a. the labeled binding reagent has an overall positive charge; and
b. the capture control reagent has an overall negative charge.

36. The test strip of claim 31, wherein the ligand is selected from the group consisting of:
a. a polypeptide, an oligopeptide, an antigen, or an antibody; or
b. a nucleic acid or a peptide nucleic acid;
c. a drug, an analog of a drug, or a drug metabolite; and
d. an imprinted polymer.

37. The test strip of claim 36, wherein the labeled binding reagent and the ligand are selected from the group consisting of:
a. the labeled binding reagent comprises a nucleic acid having an exposed target sequence of interest, and the ligand comprises a nucleic acid having a sequence of at least 65% complementarity to the target sequence of interest;
b. the labeled binding reagent comprises an antigen, and the ligand comprises an antibody that specifically binds to the antigen;
c. the ligand comprises an antigen, and the labeled binding reagent comprises an antibody that specifically binds to the antigen;
d. the ligand comprises an oligopeptide, and the labeled binding reagent comprises a protein that binds to the oligopeptide; and
e. the ligand comprises an imprinted polymer, and the labeled binding reagent comprises a substance that binds to the imprinted polymer.

38. The test strip of claim 1, wherein either the capture test reagent or the capture control reagent further comprises a solid support to which a ligand is attached, wherein:
a. the capture test reagent ligand comprises the portion of the capture test reagent that specifically binds either to the analyte or to the first complex; or
b. the capture control reagent ligand comprises the portion of the capture control reagent that binds to the labeled binding reagent.

39. The test strip of claim 38, wherein the solid support comprises latex, silica, glass, alumina, cellulose, or a sugar.

40. The test strip of claim 39, comprising at least one of the following:
a. the capture test reagent comprises a solid support comprising a capture test bead; or
b. the capture control reagent comprises a solid support comprising a capture control bead.

41. The test strip of claim 40, wherein:
a. the capture test bead or the capture control bead comprises a sulfate terminated latex bead that physically binds proteins; or
b. the capture test bead or the capture control bead comprises a covalent binding latex bead.

42. The test strip of claim 40, wherein the size of the capture test bead or the capture control bead largely inhibits its movement through the matrix.

43. The test strip of claim 40, wherein the size of the capture test bead or the capture control bead is in the range of 20% to 70% of the average pore size of the matrix.

44. The test strip of claim 40, wherein the size of the capture test bead or the capture control bead is in the range of 30% to 60% of the average pore size of the matrix.

45. The test strip of claim 40 wherein
a. the average pore size of the matrix is in the range of 4.0 to 6.0 micrometers; and b. the capture test bead or the capture control bead comprises a latex bead having a diameter in the range of 1.5 to 2.5 nanometers.

46. The test strip of claim 38, wherein the capture test reagent comprises a capture test bead and a ligand that specifically binds to the analyte or to the first complex, and wherein the binding of the ligand to the analyte or to the first complex concentrates the labeled binding reagent to enable detection of the label indicating the presence of the second complex.

47. The test strip of claim 46, wherein the capture test bead comprises a latex capture bead comprising an agglutinating agent.

48. The test strip of claim 47, wherein the agglutinating agent comprises polyethylene glycol (PEG).

49. The test strip of claim 38, wherein the capture control reagent further comprises a capture control bead, which comprises a latex capture bead comprising an agglutinating agent.

50. The test strip of claim 49, wherein the agglutinating agent comprises polyethylene glycol (PEG).

51. The test strip of claim 1, wherein the labeled binding reagent is selected to bind specifically to an analyte in blood, plasma; serum; mucus; urine; saliva; semen; vaginal discharge; sweat; tears; lymph; gastrointestinal fluid, suspension or colloidal mixture; cerebrospinal fluid; a bacterial culture; a tissue culture; a phage lysate; water; a beverage; an organic solvent; an aqueous or organic solution; a suspension of cells, viruses, or other replicative entities; or a colloidal mixture.

52. The test strip of claim 1, wherein the labeled binding reagent specifically binds to an analyte selected from the group consisting of a polypeptide, an oligonucleotide, an antibody, an antigen, a prion, a nucleic acid, a drug, and an analog of a drug.

53. The test strip of claim 1, wherein the labeled binding reagent is selected to bind specifically to an analyte, the presence or absence of which comprises a marker for a physiological condition.

54. The test strip of claim 53, wherein the physiological condition comprises pregnancy, nursing, a disease, a phenotype, a genotype, or an abnormal physiological condition.

55. The test strip of claim 1, wherein the labeled binding reagent specifically binds to an analyte comprising a drug or an analog of a drug.

56. The test strip of claim 1, wherein:
a. the labeled binding reagent comprises a monoclonal mouse anti-human chorionic gonadotropin antibody; and
b. the capture control reagent comprises a non-human, non-murid mammalian anti-mouse antibody.

57. A device for detecting the possible presence of an analyte in a liquid sample, wherein the device comprises:
a. the test strip of claim 1;
b. a housing containing the test strip, wherein the housing comprises:
i. at least one opening to expose the surface of the test strip in the application zone for application of the liquid sample;
ii. an opening to expose the surface of the test strip in the capture test zone and capture control zone for detection of test results; and
iii. indicia identifying the sample application zone, the capture test zone, and the capture control zone.

58. A method of using a test strip to detect the possible presence of an analyte in a liquid sample applied to the test strip, wherein the method comprises:
a. providing the test strip of claim 1;
b. obtaining a liquid sample;

c. applying the liquid sample to the sample application zone of the test strip;
d. wicking the liquid sample through the single hydrophilic matrix to the conjugate release zone;
e. contacting the labeled binding reagent with the liquid sample to mobilize the labeled binding reagent and to permit formation of the first complex if the liquid sample comprises analyte;
f. wicking the liquid sample and the labeled binding reagent, whether alone or in the first complex, through the single hydrophilic matrix to the capture test zone;
g. contacting the capture test reagent with the liquid sample and the labeled binding reagent, whether alone or in the first complex, to permit formation of the second complex if the first complex is present;
h. concentrating the second complex in the network of fibers in the capture test zone of the single hydrophilic matrix;
i. detecting the presence of the second complex in the capture test zone;
j. wicking the liquid sample and the labeled binding reagent through the single hydrophilic matrix to the capture control zone;
k. contacting the capture control reagent with the liquid sample and the labeled binding reagent to permit formation of the third complex;
l. concentrating the third complex in the network of fibers in the capture control zone of the single hydrophilic matrix; and
m. detecting the presence of the third complex in the capture control zone.

59. The test strip of claim 7, wherein the wicking rate is in the range of at least 4 cm in 75 seconds for water.

\* \* \* \* \*